(12) United States Patent
Chan et al.

(10) Patent No.: US 10,030,221 B2
(45) Date of Patent: Jul. 24, 2018

(54) MICROTITER PLATES FOR CONTROLLED RELEASE OF CULTURE COMPONENTS TO CELL CULTURES

(71) Applicant: Danisco US Inc., Palo Alto, CA (US)

(72) Inventors: Jimmy Chan, Mountain View, CA (US); Rachel E. Muir, Redwood City, CA (US); William Throndset, Raleigh, NC (US)

(73) Assignee: DANISCO US INC., Palo Alto, CA (US)

( * ) Notice: Subject to any disclaimer, the term of this patent is extended or adjusted under 35 U.S.C. 154(b) by 320 days.

(21) Appl. No.: 14/416,044

(22) PCT Filed: Sep. 20, 2013

(86) PCT No.: PCT/US2013/061051
§ 371 (c)(1),
(2) Date: Jan. 20, 2015

(87) PCT Pub. No.: WO2014/047520
PCT Pub. Date: Mar. 27, 2014

(65) Prior Publication Data
US 2015/0147768 A1  May 28, 2015

Related U.S. Application Data

(60) Provisional application No. 61/703,394, filed on Sep. 20, 2012.

(51) Int. Cl.
| | | |
|---|---|---|
| *C12Q 1/34* | (2006.01) |
| *C12M 1/22* | (2006.01) |
| *C12M 3/00* | (2006.01) |
| *C12M 1/12* | (2006.01) |
| *C12M 1/32* | (2006.01) |
| *C12M 1/00* | (2006.01) |
| *B29C 33/00* | (2006.01) |
| *B29C 39/02* | (2006.01) |
| *C12N 1/20* | (2006.01) |
| *C12Q 1/02* | (2006.01) |
| *B29K 83/00* | (2006.01) |
| *B29L 31/00* | (2006.01) |

(52) U.S. Cl.
CPC ......... *C12M 25/06* (2013.01); *B29C 33/0033* (2013.01); *B29C 39/02* (2013.01); *C12M 23/12* (2013.01); *C12M 29/00* (2013.01); *C12N 1/20* (2013.01); *C12Q 1/02* (2013.01); *C12Q 1/34* (2013.01); *B29K 2083/00* (2013.01); *B29L 2031/757* (2013.01)

(58) Field of Classification Search
None
See application file for complete search history.

(56) References Cited

U.S. PATENT DOCUMENTS

| | | |
|---|---|---|
| 4,673,577 A | 6/1987 | Patel |
| 4,885,175 A | 12/1989 | Zibell |
| 5,847,276 A | 12/1998 | Mimken et al. |
| 7,919,299 B2 | 4/2011 | Dunn-Coleman et al. |
| 8,685,702 B2 | 4/2014 | Muir et al. |
| 2005/0054101 A1* | 3/2005 | Felder .................... C12M 25/16 435/383 |
| 2009/0104655 A1 | 4/2009 | Buchs et al. |
| 2009/0190135 A1* | 7/2009 | Clarizia ............... C12N 5/0068 356/432 |
| 2010/0099164 A1 | 4/2010 | Vasala et al. |
| 2010/0273262 A1* | 10/2010 | Wu ........................ C12M 23/12 435/397 |
| 2010/0291045 A1 | 11/2010 | Jia et al. |
| 2011/0045571 A1 | 2/2011 | Ferrari et al. |
| 2011/0046422 A1 | 2/2011 | McAuliffe et al. |
| 2012/0045836 A1 | 2/2012 | Neubauer et al. |

FOREIGN PATENT DOCUMENTS

| | | |
|---|---|---|
| EP | 2130906 | 12/2009 |
| WO | 2004/098764 | 11/2004 |
| WO | 2005/047863 | 5/2005 |
| WO | 2008/104587 | 9/2008 |
| WO | 2010/148150 | 12/2010 |
| WO | 2011/038019 | 3/2011 |
| WO | WO 2011/073536 | * 6/2011 .............. C12M 3/00 |

OTHER PUBLICATIONS

Huber et al (Biotechnol. Bioeng., 103:1095-1102 (2009).*
Gao et al (J. Appl. Polym. Sci., 90:658-666 (2003).*
Wu et al (JACS, 125:554-559 (2003).*
Wang et al., Cytometry, 71A:866-874 (2007).*
International Search Report dated Dec. 12, 2013, for PCT Patent Application No. PCT/US2013/061051, filed on Sep. 20, 2013, 12 pages, 12.
Gene expression and characterization of isoprene synthase from Populus alba, Apr. 7, 2005, Sasaki, et al, FEBS Letters, 2514-251, 579/11.
Fed-batch mode in shake flasks by slow-release technique, Oct. 20, 2006, Jeude, et al., Biotechnol Bioeng, 433-445, 95.
Enzyme controlled glucose auto-delivery for high cell density cultivations in microplates and shake flasks, Nov. 18, 2008, Panula-Perala, et al., Microbial Cell Factories, Biomed Central, London, 1-12, 7/31.

* cited by examiner

Primary Examiner — Thomas J. Visone

(57) ABSTRACT

The invention provides a culture plate made from a polymer incorporating a culture component releasable into culture media in the well, methods of culturing a microorganisms in the culture plate, and a methods of making the culture plate.

28 Claims, 24 Drawing Sheets

MICROTITER PLATES FOR CONTROLLED RELEASE OF CULTURE COMPONENTS TO CELL CULTURES

CROSS-REFERENCE TO RELATED APPLICATIONS

This application is a U.S. National Stage Application of International Application No. PCT/US2013/061051, filed Sep. 20, 2013, which claims benefit to U.S. provisional patent application No. U.S. Ser. No. 61/703,394, filed on Sep. 20, 2012, the contents of which are hereby incorporated by reference in their entireties.

BACKGROUND

Microtiter plates are often used to incubate and culture a heterologous library of cells, or strains. For example, a library of 96 strains of cells can be compared in a single 96-well microtiter plate by culturing a different strain in each well. Thus, differences between the cells (e.g., growth rate, carbon utilization, population density, viability, protein production rate, and resistance to antibiotics) can be observed in a small format. In conventional microtiter plates, a fixed amount of carbon and other nutrients are typically batch provided to the cultured cells. As the cells grow, one or more of the nutrients can rapidly be limited or exhausted and cause the cells to slow or halt growth before differences between the cells can be observed. Thus, conventional microtiter plates are not well suited for screening libraries of cells.

To address issues with carbon limitation in conventional microtiter plates, a slow-release system for glucose delivery, the "Feedbead®" technology (Jeude et al., Biotechnol Bioeng 95:433-445, 2006), was developed for preparing pre-cultures. Feedbead® discs (AdolfKühner AG) are silicone discs embedded with sugar. Feedbead® discs, however, have several limitations. First, only relatively small amounts of sugar can be packed into such solid phases. Second, the total amount of sugar available to the culture is limited by the geometry of the disc (the discs do not contain enough carbon for sustained production). Third, the sugar release rate from such a solid phase is fastest at the beginning of the cultivation, when the amount of cells is lowest and the risk for overflow metabolism is highest. Fourth, the approach has limited scalability due to, e.g., the amount of sugar that can be packed into the beads and the lack of means to accurately control the sugar release. Finally, the presence of the Feedbead® discus or other immobilized controlled release systems (e.g., coatings, attachments) in the well interferes with bulk pipetting in screening applications. For these reasons, the technique has mostly been limited to pre-cultures (Huber et al., Biotechnol Bioeng 103:1095-1102, 2009).

SUMMARY OF THE CLAIMED INVENTION

Figure 1A:
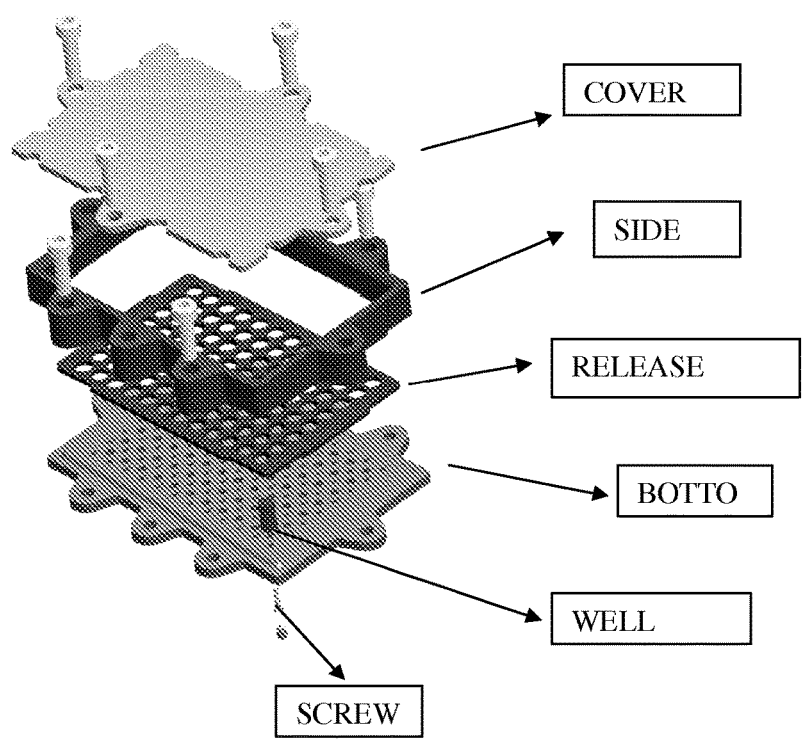
FIG. 1: (A) Diagram of a CNC Machined Mold for a 96 Well Controlled-Release polydimethylsiloxane (PDMS) Microtiter Plate; (B) 96 well post mold; (C) 24 well post mold; (D) Mold Cover with Air Lines. The positive lines in the aluminum mold become half-channels in the bottom of the PDMS srMTP, which are then sealed with a high-tack acrylic membrane. The air lines allow flow of oxygen under the plate, which diffuses through the 400 micron-thick area under each well, to improve the oxygen transfer rate to the growing cells.

The invention provides a culture plate having a culture well, wherein the plate is made of a polymer incorporating a culture component releasable into culture media in the well. Optionally, the plate consists essentially of the polymer incorporating the culture component or the culture well consists essentially of the polymer incorporating the culture component. Optionally, the plate is a unitary piece formed from the polymer incorporating the culture component, wherein the polymer is formed by polymerization of a monomer in a mold. Optionally, the plate is a monolith. Some such culture plates are microtiter plates, having e.g., at least 24 or 96 wells. The culture component can be a nutrient, such as a sugar, e.g., glucose. The concentration of glucose can be 15%-25% or 17.5%-22.5% or 20% by weight with respect to the polymer. The culture component can also be an antibiotic or buffer. The polymer can be a silicone polymer, such as polydimethylsiloxane (PDMS). In some culture plates one or more wells are connected to air lines molded into the culture plate.

The invention further provides a method of culturing a cell, comprising culturing the cell in a well of a culture plate as described above, whereby the culture component is released into the well as the cell is cultured. Optionally the plurality of cells are cultured in a plurality of wells of the microtiter plate. Optionally the culture media is free of the culture component except as released into the culture media from the polymer. Optionally the culture component is released over at least 48 hrs. Optionally, the method further comprises comparing production of a protein or other metabolite by cells from the plurality of wells. Optionally, the method further comprises comparing the growth rates of the cells from the plurality of wells. Optionally, the method further comprises selecting a cell based on above average growth rate or above average production. For instance, the method further comprises selecting a cell based on above average production of a protein or metabolite. In some methods, the growth rate or protein/metabolite production of different strains or variants of cells is compared. In some methods, the growth rate or protein/metabolite production of the cells in different culture media is compared. Some methods further comprise transferring the culture from the well into a larger volume culture. Optionally, the larger volume culture is a fed-batch culture or a batch culture.

The invention further provides a mold for forming a culture plate, the mold comprising: a plurality of elongate well posts; a bottom plate having a plurality of recess portions, each of the recess portions being configured to receive and support one of the plurality of elongate well posts; a release plate containing a plurality of holes, each of the holes being configured to receive there-through at least a portion of one of the plurality of elongate well posts; a side wall plate having a plurality wall portions, the wall portions being configured to substantially surround the plurality of elongate well posts; and a cover plate, wherein the side wall plate and the release plate are positioned substantially intermediate the cover plate and the bottom plate so as to define an interior cavity occupied by at least the release plate and the plurality of elongate well posts. Optionally, at least the cover plate, the side wall plate, and the bottom plate comprise a plurality of holes; and each of the plurality of holes being configured to receive a screw so as to securely affix at least the cover plate, the side wall plate, and the bottom plate relative to one another and hold the mold together. Optionally, the bottom plate further comprises a plurality of channels to form a plurality of air lines. Optionally, the plurality of air lines is configured to facilitate diffusion of a flow of air, oxygen, or other gas to a portion of each of the plurality of well posts.

The invention further provides a method of forming a culture plate, comprising assembling a mold as defined above; introducing a monomer, culture component and polymerization initiator into the mold, wherein polymerization occurs, thereby forming a polymer between the cover plate, the side plate, and the release plate; and dissembling the mold, wherein separation of the polymer from the wells posts generates wells of the culture plate.

DEFINITIONS

A culture plate that is a unitary piece or monobody means that all parts are contiguous such as when formed by polymerization of a monomer (plus culture component) in a mold or by solidification of a liquid polymer using a cross-linking agent in a mold.

A monolith culture plate is formed by assembling components of a culture plate, each component being formed by polymerization as described above for a monobody. Preferably each component is formed from the same monomer and curing agent. The culture component can be the same or different in different components as can its concentration. The components are joined by curing such that covalent bonds form between polymers in the components. For example, the components of a monolith can be layers or sections of the culture plate. Although the exterior appearance of a monolith may not be distinguishable to the eye from a monolayer, the joins between components are visible at least microscopically (e.g., with an electron microscope) when viewing a cross-section of the monolith.

"Consisting essentially of" is used in accordance with convention to define the basic and novel features of an object. Thus, a culture plate consisting essentially of a polymer means that the polymer is a predominant component of the culture plate responsible for its essential functions but does not preclude the addition of accessory parts not made of the polymer, such as labeling, decoration or a handle.

A "metabolite" is a compound, substance, byproduct, intermediate, or product derived from the metabolic processes in a cell.

"Batch culture" is a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

"Fed-batch culture" is a method of culturing cells in which additional components are provided to the culture at some time subsequent to the beginning of the culture process. The provided components typically comprise nutritional supplements for the cells which have been depleted during the culturing process. A fed-batch culture is typically stopped at some point and the cells and/or components in the medium are harvested and optionally purified.

The term "monomer" refers to any chemical entity that is capable of reacting with like molecules and thereby forming a larger entity comprising more than one of the original monomers (e.g., a polymer). Thus, a "monomer" also encompasses an "oligomer" still capable of undergoing a polymerization reaction. The term "polymer" refers to the product of a polymerization reaction, and is inclusive of homopolymers, copolymers, terpolymers, random polymers, graft polymers, block polymers and the like.

As used herein, the terms "controlled release" and "slow-release" may be used interchangeably. For instance, the terms "controlled release microtiter plate" or "crMTP" may be used interchangeably with "slow release microtiter plate" or "srMTP". Controlled release, or slow release, microtiter plates are in contrast to conventional microtiter plates (cMTP).

DETAILED DESCRIPTION

I. General

The invention provides a culture plate containing one or more culture wells (e.g., a microtiter plate) made from a polymer incorporating a culture component releasable into culture media in the well. Unlike Feedbead® discs which are suspended in the culture media or immobilized or otherwise attached on the walls or bottoms of the plate wells (e.g., as a coating or lining), the whole body of a culture plate can be made of a polymer matrix incorporating a culture component. Such a culture plate can be made, e.g., by casting the entire plate using a polymer embedded with a culture component or components.

As compared to other culture component release systems such as Feedbead® discs (AdolfKühner AG), the present culture plate has significantly improved surface area to volume ratio, capable of providing a virtually unlimited reservoir of the culture component within the normal range of culture times used for production hosts. The surface areas of the present culture plate remain constant or increase slightly (e.g., channels inside the matrix) over the time. Consequently, the release rate of culture component using the present culture plate remains constant or increases over the time (e.g., slowest at the beginning of the fermentation). By contrast, the release rate of Feedbead® discs decreases over time due to depletion of the available amount of culture component.

In conventional batch culture systems cellular physiology dissimilar to that of fed-batch culture systems is observed. The present culture plate can, however, provide cultures having cellular physiology more analogous to that of fed-batch culture systems (e.g., bioreactors or large scale production systems. As a result, the expression profile in the present culture plate is similar to that in fed-batch culture systems. The protein production obtained in the present culture plate is thus more reproducible on transfer and scale-up to fed-batch culture systems, such as industrial-scale fermentation processes.

In conventional culture systems or culture component release systems, unequal growth kinetics are observed for cultures of different strains or variants. The present culture plate can circumvent or at least minimize this problem, resulting in normalization of growth in various strains and variants. In addition, proteins can be consistently produced in high concentrations. Proteins produced in the plate can be used directly in downstream applications, obviating the needs for concentrating lysates or supernatants. Additionally, culture time can be extended, enabling detection of larger absolute differences in titers between strains that produce products at different rates (i.e., g/L/hour). The present culture plate is therefore useful in screening strains with improved enzyme production capacity, process optimization, media formulation and optimization, and screening molecule libraries.

II. Culture Plates

A culture plate can have different shapes and dimensions. A culture plate generally includes a substantially flat surface with wells extending down from the surface to enclose individual cultures. Suitable shapes for the flat surface include circular, rectangular, quadratic, polygonal, among others. Corners can be rounded or square.

The wells can be viewed as having a bottom and a wall contiguous with and extending upwardly from the bottom, forming the well. Some wells have a substantially flat bottom and vertical walls. Other wells have a conical shape in which case there may be no clear demarcation between the bottom and the wall. The wells can be any shape such as substantially circular or substantially rectangular. The wells can also include one or more features or shapes to facilitate, for example, mixing or aeration of the liquid culture. For example, the wells can include baffles along the bottom or sides of the wells.

Culture plates can be functionalized with one or more channels. Some culture plates contain channels for delivering air or oxygen into wells of culture plates (i.e., "air lines"). Some culture plates contain channels in the bottom of the plates, through which air or oxygen diffuses into each well. Some culture plates (e.g., a micro and/or nano-scale device such as a microfluidic device and/or microtiter plate) contain at least one microscale or nanoscale channels.

The present culture plate can have one or more wells, e.g., 4, 6, 8, 12, 24, 48, 96, 384 or 1536 wells per plate or more wells per plate. Usually all wells on a plate are substantially identical (as manufacturing tolerance allows). The maximum volume of one well depends on the dimensions of the plate, the number of wells, and the height of wells. Sizes of standard microtiter plates and dimensions of the wells are well-known. In some 96-well plates, the maximum volume of one well is about 500 µl. In some 384-well plates, the maximum volume of one well is about 50 µl. Plates having wells of maximum volume less than 1 ml and usually no more than 500 µl are considered microtiter plates. For example, a conventional 96-well plate is often referred to as a microtiter plate. Plates having wells of maximum volume less than 1 µl are referred to as nanotiter plates.

Culture plates can be made in accordance with standardized measurements for well spacing, depth, and diameter among others as proposed by American National Standards Institute (ANSI) in 2003.

The culture plate can be provided sterile, free of DNase, RNase, or pyrogen or in any combination thereof.

III. Polymer Matrix

The present culture plate is made from a polymer matrix embedded with a culture component or components. The polymer can be combined with the culture component by physical or chemical means, e.g., by interspersing the culture component into the polymer material. The entire interior surface of the culture wells (e.g., the bottom and walls) thus constitutes the polymer matrix. For example, the present culture plate can be manufactured by polymerizing a monomer within a mold or by cross-linking and solidifying a liquid polymer within a mold. Other molding techniques, such as injection molding, embossing or stamping, can be used. Preferably, the culture plate consists essentially of the polymer and embedded culture component, and more preferably is a unitary piece or monobody of the polymer and embedded culture component. In cases where multiple layers of the plate are poured separately, and then bonded together, additional features may be added. Such systems may be fabricated as a multi-component structure of two or more components. The two or more components may have any suitable relative spatial relationship and may be attached to one another by any suitable bonding mechanism. Additionally, the culture plate can be manufactured with more than one layer, which are then cured into a single monolith (i.e., "multilayer lithography"). These layers can contain the same or different culture components. Furthermore features including but not limited to pumps and valves, air lines, lenses, and sensors can be incorporated into such culture plates. Additionally, in some cases the culture plate can be manufactured with an optically clear bottom layer for use in instruments such as spectrophotometers, inverted microscopes, and/or plate scanners. In some cases this bottom layer may or may not contain any culture component. In other cases, a culture plate can be manufactured without a bottom, and subsequently bonded in a multitude of ways to optical quality glass or quartz, plastic or any suitable material to facilitate analysis of the well contents by various types of instrumentation. Because excess amounts of culture component can be embedded in and released from the polymer, culture plates of the present invention can be used without linings or particles of embedded polymers.

Culture components with a wide particle-size distribution (e.g., 1 µm to 5 mm, 5 µm to 2 mm, more preferably 50-500 µm) can be incorporated into the polymer matrix. Preferably, particles with a uniform size distribution or narrow size distributions are used, with which culture component can be released with defined kinetics. Particles with different defined-size distributions or mixtures of two or more fractions, each with a narrow particle size distribution, can also be used. Particles can be either crystalline or amorphous. Additionally, liquid microdroplets can be incorporated into the culture plates, in some cases facilitated by emulsification, depending on factors such as the charge of the component being added to the plate, which for example can affect hydrophobicity.

Culture components can be embedded in the polymer matrix in various concentrations (e.g., 0.1%-60%, 1%-40%, more preferably 10%-30% by weight. Concentrations are determined weight for weight for the culture component compared with the total weight of the polymerization mix (e.g., culture component, monomer and curing agent) prepolymerization. The desired concentrations can vary considerably depending on the culture components used. When nutrients such as carbon sources (e.g., glucose) are used, the concentration is generally at least 1%, 2%, 5%, 10%, and up to 5%, 10%, 15%, 20%, 25%, 30%, 35%, 40%, 45%, 50% by weight including all permutations and combinations of lower and upper limits. For example, glucose concentration can be about 5%, 10%, 15%, 20%, 25%, 30%, 35%, 40%, 45%, 50% by weight. A preferred glucose concentration is 15%-30%, preferably 15%-25%, more preferably 17.5%-22.5%, by weight. Other culture components such as antibiotics or minerals can be present in much lower concentrations, e.g., 0.1%-5% by weight. The concentrations referred to are initial concentrations and decrease as the culture component is released to the culture media. Two or more culture components can be embedded in the same polymer matrix.

The culture component is releasable from the culture plate into the culture media within the wells of the plate. The proportion of culture component released can be at least 1%, 5%, 10%, 20%, 30%, 40%, 50%, 60%, 70%, 80%, 90%, 95%, 99% of the culture component associated with the culture plate or its constituent polymer. The culture component may or may not be subject to degradation (e.g., conversion of cellulose to glucose) within the culture plate before release or in culture media after release. Typically, the culture component is released in soluble form. The culture component incorporated into the polymer matrix can be released over a period of time ranging from a minimum of an hour to a maximum of several weeks. For example, the culture component can be released over at least 1, 5, 10, 24, 36, 48, 72 hours. In some cultures, the culture component is released over at least 1, 2, 3, 4, 5 weeks.

The release of the culture components can be retarded, i.e., the culture components can be supplied to the culture media after a certain delay from the start of the fermentation. The retardation allows for adapting the supply to a lag phase of the microorganisms or cells. For example, the release can be delayed by coating the wells of the culture plate with a water-soluble or water-insoluble coating that does not contain the desired culture component. The coating retards the release of the culture components from the polymer matrix. Such coatings include water-soluble or permeable compositions such as hydroxypropyl methyl cellulose, sugars and the like. Depending on the thickness and porosity of the water-soluble or permeable coatings, such coatings retard the release of the culture components in the polymer matrix by first requiring the coating to dissolve before the culture components are released. Suitable water-insoluble coatings include water-insoluble polymers (e.g., polyvinyl acetate), food grade shellac (see, e.g., U.S. Pat. No. 4,673,577), water insoluble wax coatings (see, e.g., U.S. Pat. No. 4,885,175), zein, and fatty acids. Suitable coatings also include proteins such as casein, starches, dextrins, modified or unmodified cellulosics (e.g., ethyl, methyl, hydroxypropyl, hydroxyethyl cellulose), gum arabic, fats, carbohydrates, and silica.

Polymers

Natural and synthetic polymers can be used as polymer materials for the polymer matrix. Suitable polymer materials include plastics, such as polydimethylsiloxane (PDMS), polymethylmethacrylate (PMMA), polycarbonate, polytetrafluoroethylene (TEFLON™), polyvinyl, polyvinylchloride (PVC), polysulfone, polystyrene, polymethylpentene, polypropylene, polyethylene, polyvinylidine fluoride, ABS (acrylonitrile-butadiene-styrene copolymer), and the like. Suitable polymer materials also include polysaccharides and their derivatives; polysiloxanes; polyacrylic acid and its derivatives; polycarbonates; polyolefins and their derivatives; polycarboxylic acids and their derivatives; polyethers and their derivatives; polyesters and their derivatives; polyamines and amides and their derivatives; polysulfones and their derivatives; polyurethanes; polyvinyls and their derivatives, especially polyvinyl alcohols. Suitable polymer materials also include copolymers of the polymers cited above and derivatives obtained by modification. Polymerization can be effected by contacting a solution of monomers and culture component(s) with a polymerization initiator. A liquid polymer can also be solidified by a cross-linking agent. Suitable polymer materials also include agar, agarose, and for example low-melting-temperature agarose. Suitable polymer materials also include gelatin and functionalized derivatives thereof.

The polymer or polymers used in the polymer matrix can be used in various concentrations, and are determined weight for weight. The desired concentrations can vary considerably depending on the polymer or polyumers used. For example, the concentration of polymer or polymers used can be at least 1%, 2%, 5%, 10%, 20%, 25%, 30%, 40%, 50%, 60%, 70%, 75%, 80%, 90%, 99%, 99.9% or more by weight including all permutations and combinations of lower and upper limits.

Culture Components

Various culture components can be embedded in the polymer matrix. Such culture components include components that are consumed by cell growth (e.g., nutrients). Examples of such components include various nutrients for cell growth, include carbon sources (e.g., sugars), minerals, and salts.

Suitable carbon sources include carbohydrates (such as monosaccharide, disaccharide, oligosaccharide, or polysaccharides), yeast extract or one or more components of yeast extract. Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

Suitable salts and minerals include nitrogen-containing materials (e.g., nitrate salts, ammonium salts), phosphorus-containing materials (e.g., phosphate salts), sodium salts, potassium salts, calcium salts, magnesium salts, and sulfur-containing salts (e.g., sulfate salts). Other salts and minerals include iron, manganese, zinc, boron, chloride, iodine, copper, cobalt, and molybdenum containing materials. Other culture components suitable for the polymer matrix include various buffers (e.g., phosphate, citrate, succinate, malate), cofactors, vitamins (e.g., thiamin, nicotinic acid, pyridoxine, myo-inositol), amino acids or other nitrogen supplements, antibiotics (e.g., ampicillin, gentamicin, streptomycin, neomycin and polymyxin B), protein expression inducers (e.g., Isopropyl-β-D-thio-galactoside), polypeptides and proteins (e.g., enzymes), and small molecule drugs (e.g., for screening drug candidates). Exemplary culture components suitable for the polymer matrix include 5-aminosalicylates, 5HT3 receptor antagonists, adamantane antivirals, adrenal cortical steroids, adrenal corticosteroid inhibitors, adrenergic bronchodilators, agents for hypertensive emergencies, agents for pulmonary hypertension, aldosterone receptor antagonists, alkylating agents, alpha-glucosidase inhibitors, alternative medicines, amebicides, aminoglycosides, aminopenicillins, aminosalicylates, amylin analogs, analgesic combinations, analgesics, androgens and anabolic steroids, angiotensin converting enzyme inhibitors, angiotensin II inhibitors, anorectal preparations, anorexiants, antacids, anthelmintics, anti-angiogenic ophthalmic agents, anti-CTLA-4 monoclonal antibodies, anti-infectives, antiadrenergic agents, centrally acting, antiadrenergic agents, peripherally acting, antiandrogens, antianginal agents, antiarrhythmic agents, antiasthmatic combinations, antibiotics/antineoplastics, anticholinergic antiemetics, anticholinergic antiparkinson agents, anticholinergic bronchodilators, anticholinergic chronotropic agents, anticholinergics/antispasmodics, anticoagulants, anticonvulsants, antidepressants, antidiabetic agents, antidiabetic combinations, antidiarrheals, antidiuretic hormones, antidotes, antiemetic/antivertigo agents, antifungals, antigonadotropic agents, antigout agents, antihistamines, antihyperlipidemic agents, antihyperlipidemic combinations, antihypertensive combinations, antihyperuricemic agents, antimalarial agents, antimalarial combinations, antimalarial quinolines, antimetabolites, antimigraine agents, antineoplastic detoxifying agents, antineoplastic interferons, antineoplastics, antiparkinson agents, antiplatelet agents, antipseudomonal penicillins, antipsoriatics, antipsychotics, antirheumatics, antiseptic and germicides, antithyroid agents, antitoxins and antivenins, antituberculosis agents, antituberculosis combinations, antitussives, antiviral agents, antiviral combinations, antiviral interferons, anxiolytics, sedatives, and hypnotics, aromatase inhibitors, atypical antipsychotics, azole antifungals, bacterial vaccines, barbiturate anticonvulsants, barbiturates, BCR-ABL tyrosine kinase inhibitors, benzodiazepine anticonvulsants, benzodiazepines, beta-adrenergic blocking agents, beta-lactamase inhibitors, bile acid sequestrants, biologicals, bisphosphonates, bone resorption inhibitors, bronchodilator combinations, bronchodilators, calcineurin inhibitors, calcitonin, calcium channel blocking agents, carbamate anticonvulsants, carbapenems, carbonic anhydrase inhibitor anticonvulsants, carbonic anhydrase inhibitors, cardiac stressing agents, cardioselective beta blockers, cardiovascular agents, catecholamines, central nervous system agents, cephalosporins, cerumenolytics, CFTR potentiators, chelating agents, chemokine receptor antagonist, chloride channel activators, cholesterol absorption inhibitors, cholinergic agonists, cholinergic muscle stimulants, cholinesterase inhibitors, CNS stimulants, coagulation modifiers, colony stimulating factors, contraceptives, corticotropin, coumarins and indandiones, cox-2 inhibitors, decongestants, dermatological agents, diagnostic radiopharmaceuticals, dibenzazepine anticonvulsants, digestive enzymes, dipeptidyl peptidase 4 inhibitors, diuretics, dopaminergic antiparkinsonism agents, drugs used in alcohol dependence, echinocandins, EGFR inhibitors, estrogen receptor antagonists, estrogens, expectorants, factor Xa inhibitors, fatty acid derivative anticonvulsants, fibric acid derivatives, first generation cephalosporins, fourth generation cephalosporins, functional bowel disorder agents, gallstone solubilizing agents, gamma-aminobutyric acid analogs, gamma-aminobutyric acid reuptake inhibitors, gastrointestinal agents, general anesthetics, genitourinary tract agents, GI stimulants, glucocorticoids, glucose elevating agents, glycopeptide antibiotics, glycoprotein platelet inhibitors, glycylcyclines, gonadotropin releasing hormones, gonadotropin-releasing hormone antagonists, gonadotropins, group I antiarrhythmics, group II antiarrhythmics, group III antiarrhythmics, group IV antiarrhythmics, group V antiarrhythmics, growth hormone receptor blockers, growth hormones, H. pylorieradication agents, H2 antagonists, hedgehog pathway inhibitors, hematopoietic stem cell mobilizer, heparin antagonists, heparins, HER2 inhibitors, herbal products, histone deacetylase inhibitors, hormones, hormones/antineoplastics, hydantoin anticonvulsants, illicit (street) drugs, immune globulins, immunologic agents, immunostimulants, immunosuppressive agents, impotence agents, in vivo diagnostic biologicals, incretin mimetics, inhaled anti-infectives, inhaled corticosteroids, inotropic agents, insulin, insulin-like growth factor, integrase strand transfer inhibitor, interferons, interleukin inhibitors, interleukins, intravenous nutritional products, iodinated contrast media, ionic iodinated contrast media, iron products, ketolides, laxatives, leprostatics, leukotriene modifiers, lincomycin derivatives, local injectable anesthetics, loop diuretics, lung surfactants, lymphatic staining agents, lysosomal enzymes, macrolide derivatives, macrolides, magnetic resonance imaging contrast media, mast cell stabilizers, medical gas, meglitinides, metabolic agents, methylxanthines, mineralocorticoids, minerals and electrolytes, miscellaneous agents, miscellaneous analgesics, miscellaneous antibiotics, miscellaneous anticonvulsants, miscellaneous antidepressants, miscellaneous antidiabetic agents, miscellaneous antiemetics, miscellaneous antifungals, miscellaneous antihyperlipidemic agents, miscellaneous antimalarials, miscellaneous antineoplastics, miscellaneous antiparkinson agents, miscellaneous antipsychotic agents, miscellaneous antituberculosis agents, miscellaneous antivirals, miscellaneous anxiolytics, sedatives and hypnotics, miscellaneous bone resorption inhibitors, miscellaneous cardiovascular agents, miscellaneous central nervous system agents, miscellaneous coagulation modifiers, miscellaneous diuretics, miscellaneous genitourinary tract agents, miscellaneous GI agents, miscellaneous hormones, miscellaneous metabolic agents, miscellaneous ophthalmic agents, miscellaneous otic agents, miscellaneous respiratory agents, miscellaneous sex hormones, miscellaneous topical agents, miscellaneous uncategorized agents, miscellaneous vaginal agents, mitotic inhibitors, monoamine oxidase inhibitors, mouth and throat products, mTOR inhibitors, mucolytics, multikinase inhibitors, muscle relaxants, mydriatics, narcotic analgesic combinations, narcotic analgesics, nasal anti-infectives, nasal antihistamines and decongestants, nasal lubricants and irrigations, nasal preparations, nasal steroids, natural penicillins, neuraminidase inhibitors, neuromuscular blocking agents, neuronal potassium channel openers, next generation cephalosporins, nicotinic acid derivatives, NNRTIs, non-cardioselective beta blockers, non-iodinated contrast media, non-ionic iodinated contrast media, non-sulfonylureas, nonsteroidal anti-inflammatory agents, nucleoside reverse transcriptase inhibitors (NRTIs), nutraceutical products, nutritional products, ophthalmic anesthetics, ophthalmic anti-infectives, ophthalmic anti-inflammatory agents, ophthalmic antihistamines and decongestants, ophthalmic diagnostic agents, ophthalmic glaucoma agents, ophthalmic lubricants and irrigations, ophthalmic preparations, ophthalmic steroids, ophthalmic steroids with anti-infectives, ophthalmic surgical agents, oral nutritional supplements, other immunostimulants, other immunosuppressants, otic anesthetics, otic anti-infectives, otic preparations, otic steroids, otic steroids with anti-infectives, oxazolidinedione anticonvulsants, parathyroid hormone and analogs, penicillinase resistant penicillins, penicillins, peripheral opioid receptor antagonists, peripheral vasodilators, peripherally acting antiobesity agents, phenothiazine antiemetics, phenothiazine antipsychotics, phenylpiperazine antidepressants, plasma expanders, platelet aggregation inhibitors, platelet-stimulating agents, polyenes, potassium-sparing diuretics, probiotics, progesterone receptor modulators, progestins, prolactin inhibitors, prostaglandin D2 antagonists, protease inhibitors, proton pump inhibitors, psoralens, psychotherapeutic agents, psychotherapeutic combinations, purine nucleosides, pyrrolidine anticonvulsants, quinolones, radiocontrast agents, radiologic adjuncts, radiologic agents, radiologic conjugating agents, radiopharmaceuticals, recombinant human erythropoietins, renin inhibitors, respiratory agents, respiratory inhalant products, rifamycin derivatives, salicylates, sclerosing agents, second generation cephalosporins, selective estrogen receptor modulators, selective immunosuppressants, selective phosphodiesterase-4 inhibitors, selective serotonin reuptake inhibitors, serotonin-norepinephrine reuptake inhibitors, serotoninergic neuroenteric modulators, sex hormone combinations, sex hormones, skeletal muscle relaxant combinations, skeletal muscle relaxants, smoking cessation agents, somatostatin and somatostatin analogs, spermicides, statins, sterile irrigating solutions, streptomyces derivatives, succinimide anticonvulsants, sulfonamides, sulfonylureas, synthetic ovulation stimulants, tetracyclic antidepressants, tetracyclines, therapeutic radiopharmaceuticals, therapeutic vaccines, thiazide diuretics, thiazolidinediones, thioxanthenes, third generation cephalosporins, thrombin inhibitors, thrombolytics, thyroid drugs, TNF alfa inhibitors, tocolytic agents, topical acne agents, topical agents, topical anesthetics, topical anti-infectives, topical antibiotics, topical antifungals, topical antihistamines, topical antineoplastics, topical antipsoriatics, topical antivirals, topical astringents, topical debriding agents, topical depigmenting agents, topical emollients, topical keratolytics, topical non-steroidal anti-inflammatories, topical photochemotherapeutics, topical rubefacient, topical steroids, topical steroids with anti-infectives, triazine anticonvulsants, tricyclic antidepressants, trifunctional monoclonal antibodies, ultrasound contrast media, upper respiratory combinations, urea anticonvulsants, urinary anti-infectives, urinary antispasmodics, urinary pH modifiers, uterotonic agents, vaccine combinations, vaginal anti-infectives, vaginal preparations, vasodilators, vasopressin antagonists, vasopressors, VEGF/VEGFR inhibitors, viral vaccines, viscosupplementation agents, vitamin and mineral combinations, vitamins.

Enzyme-Based Controlled-Release

Culture components can be provided in oligomeric or polymeric forms when incorporated in the polymer matrix. Some polymers or oligomers can be directly used by certain microorganisms or cells whereas other microorganisms or cells only use monomers. When oligomeric or polymeric forms of culture components cannot be directly used by the microorganisms or cells, they can be degraded into monomers by chemicals or enzymes (see, e.g., US2012/0045836 and US2010/0099164).

When polymers or oligomers are used, the release of the monomers into the culture media can be retarded and controlled. At the beginning of the fermentation (the lag phase), the polymers or oligomers have not, or only partially, converted into monomers. The limited availability of monomers avoids the risk for overflow metabolism. When the microorganisms or cells enter production phase, more polymers or oligomers have been converted into monomers, providing a continuous supply of nutrients needed for production.

Degrading chemicals or enzymes can be incorporated into the polymer matrix in amounts sufficient for degrading the oligomers or polymers in the matrix. They can also be a component of the culture media. For example, many animal serums contain hydrolytic enzymes such as amylases and maltases that degrade starch. Alternatively, the chemicals or enzymes can be a product, a by-product, or a metabolite of the microorganisms or cells in the culture media. For example, starch can be used as a culture component when the microorganism or cell cultivated in the culture plate secrets glucoamylase or a-amylase into the media. In such cases, it is not required to have exogenous starch-degrading enzymes in the polymer matrix or in the media.

Preferred oligomers or polymers are water-soluble, partly water-soluble. Water insoluble oligomers or polymers (e.g., cellulose) can also be used. For example, the oligomeric or polymeric forms of glucose can be starch, glucan, cellulose ($\beta$-1,4-glucan), curdlan ($\beta$-1,3-glucan), dextran ($\alpha$-1,6-glucan), glycogen ($\alpha$-1,4- and $\alpha$-1,6-glucan), laminarin $\beta$-1,3- and $\beta$-1,6-glucan), lentinan $\beta$-1,6: $\beta$-1,3-glucan), lichenin, pleuran $\beta$-1,3- and ($\beta$-1,6-glucan), pullulan ($\alpha$-1,4- and $\alpha$-1,6-glucan), starch ($\alpha$-1,4- and $\alpha$-1,6-glucan), and zymosan ($\beta$-1,3-glucan), or derivatives thereof (e.g., dextrin). Examples of derivatives of glucose polymers include soluble-starch derivatives and dextrin, cellulose derivative, methylcellulose and carboxymethylcellulose, Depending on the oligomeric or polymeric forms of glucose used, a wide variety of enzymes can be used for degrading them. Both exo-enzymes and endo-enzymes or a combination thereof can be used. Exemplary enzymes include $\alpha$-amylases, glucoamylases ($\gamma$-amylases), isoamylases, $\beta$-glucosidases and other cellulolytic enzymes. When a constant glucose release is desired, exo-enzymes digesting the end (reduced or non-reduced) of the polymers or oligomers are preferred. Glucoamylases can be used for degrading glucose-polymers rich in α-1,4-linkages, whereas β-glucosidases and other cellulolytic enzymes are preferred for glucans rich in β-1,4-linkages. Debranching enzymes such as isoamylases are preferred for degrading glucans rich in alpha-1,6-linkages. α-amylases and γ-amylases can be used for degrading starch or soluble starch derivatives. Dextrin can be degraded by glucoamylases, optionally in combination with other amylases (e.g., α-amylases, isoamylases). Maltose, maltotriose and other short α-1,4-linked glucose polymers can be degraded with glucoamylase. Other enzymes useful for degrading oligomeric or polymeric forms of culture components include proteases, peptidases, nucleases and amidases.

IV. Methods of Forming a Culture Plate

Culture plate can be made using a mold. The mold can be manufactured by conventional machining processes, such as turning, boring, drilling, milling, broaching, sawing, shaping, planing, reaming, and tapping, or grinding. Additionally the mold can be manufactured, for example, by electrical discharge machining, electrochemical machining, electron beam machining, photochemical machining, and ultrasonic machining and the like. A suitable mold includes a bottom plate, a release plate, a side wall plate, and a cover plate. The bottom plate has a plurality of recess portions (e.g. indentations), each configured to receive and support at least a base of one of a plurality of well posts. The release plate contains one or more holes, each similarly configured to receive there-through at least a portion of one of the plurality of elongate well posts, when the release plate is positioned substantially adjacent (e.g., over) the bottom plate. The mold further includes a side wall plate having a plurality of wall portions, which form and define a periphery substantially defining a periphery of the mold. The side wall plate is positioned intermediate to the cover plate and the release plate. In this manner, the cover plate, the side wall plate, and the base plate cooperate to substantially surround and enclose a volume between the cover plate and the release plate. The base plate, the cover plate, and the side wall plate further comprise a plurality of holes positioned about the periphery thereof. A plurality of screws are used to occupy the plurality of holes, thereby securing the base plate, the cover plate, and the side wall plate relative to one another, thus holding the mold together. The cover plate can further comprise a plurality of channels to form a plurality of air or liquid channels in the completed part. Culture plates may be fabricated as a unitary structure from a single component, or as a multi-component structure of two or more components. In cases where multiple layers of the plate are poured separately, and then bonded together, more than one mold can be used to make each layer of the plate. The two or more layers may have any suitable relative spatial relationship and may be attached to one another by any suitable bonding mechanism. In some cases, no mold is needed for relatively thin layers, which may be poured and cut to size. In some cases the layer(s) are 10 to 100 micrometers in thickness. In some cases the layer(s) may be 20 to 50 micrometers in thickness, in other cases 50 to 300 micrometers in thickness. In yet other cases the layers may be 0.1 to 4 centimeters in thickness, or in yet other cases 0.5 cm and up to 10 cm or more in thickness.

To make a culture plate, a mixture of a monomer, one or more culture components and optionally a polymerization initiator is into a mold as described above. The components can be introduced together or separately in any order. Polymerization occurs within the mold(s), forming a polymer between the cover plate, side and release plate. The mold is then dissembled. The polymer is separated from the wells posts, generating wells of the culture plate. In cases where multiple layers of polymer are used, these are bonded together by a multitude of technologies including among others, direct polymerization of partially cured layers to one another, or by functionalization of each layer by, for example oxygen plasma treatment.

Alternatively a culture plate can be made by introducing a liquid polymer or a mixture of liquid polymers, one or more culture components and a cross-linking agent into a mold as described above. Again, the components can be introduced together or in any order. Cross-linking process occurs within the mold, solidifying the polymer between the cover plate, side and release plate. The mold is then dissembled. The solidified polymer is separated from the wells posts, generating wells of the culture plate.

V. Methods of Culturing Microorganisms and Cell Lines

The present culture plate can be used for culturing various microorganisms, cell lines or other cell cultures. Because the culture component is released into the wells as the culture grows, the releasable culture component may or may not be supplied in the culture media as well. Cells can be cultured in a media initially having culture component in amounts sufficient for the growth phase, or in a media free of the culture component except as released into the culture media from the polymer matrix. Additional amounts of culture component are released into the culture as the culture enters into the production phase.

Cells can be selected based on protein, metabolite, or biochemical production (quantity or activity), or based on growth rates. For example, in some methods, growth rates within certain time frame can be screened to select, e.g., fast-growing strains that reach the production phase in shortest time.

Moreover, the current method circumvents or at least minimizes the problem of unequal growth kinetics in cultures of different strains or variants. The controlled release of the culture component evens out the growth rate, i.e., different strains or variants all consume the same amount or at least more similar amounts of carbon due to the linear release kinetics of the controlled release culture plate. Therefore, different strains or variants have similar growth rates, induce expression around the same time, and stay in production phase for about the same period, leading to normalization of growth of various strains and variants. Observed differences in production are therefore more representative of intrinsic production capacity rather than initial growth rate. A microorganism, hybridoma, insect cell and other types of cells can therefore be selected based on the highest specific productivity of a protein or metabolite. Since the culture time can be extended beyond the normal limits of batch culture, larger absolute differences between strains or clones with different rates of specific productivity can be measured. This can enable selection of strains with smaller differences in production capacity since larger absolute differences can in some cases allow for protein or metabolite measurement outside of the noise range of a given assay.

In some embodiments, the kinetics of controlled release of the culture component into the microtiter plate wells depends on the concentration of the culture component that is molded into the microtiter plate. The concentration of the culture component can be anywhere from 0.01% to 50%, including all permutations and combinations of lower and upper limits. For instance, the concentration of the culture component can be 0.01%, 0.1%, 0.25%, 0.5%, 1%, 2%, 3%, 4%, 5%, 10%, 15%, 20%, 25%, 30%, 40%, 50%, or any percentage in between. These percentages are not intended to be limiting and are only meant for illustrative purposes. The linear release kinetics of the controlled release culture plate can be observed anywhere 0 hours to 288 hours, or any time in between including all permutations and combinations of lower and upper limits. For instance, the linear release kinetics can begin at 0, 1, 2, 3, 4, 5, 6, 7, 8, 9, 10 or more hours. The linear release kinetics may be observed as late as 50, 60, 70, 80, 90, 100, 125, 150, 175, 200, 225, 250, 275, or 288 hours. For instance, the linear release kinetics may be observed from 0-24 hours, 0-48 hours, 0-72 hours, 0-96 hours, 2-24 hours, 2-48 hours, 2-72 hours, 2-96 hours, or any other range including all permutations and combinations of lower and upper limits. These ranges are not intended to be limiting and are only meant for illustrative purposes. The linear release kinetics may depend on the culture component molded into the microtiter plate.

The current method can also be used to select an optimal culture media for protein, metabolite, or biochemical production or growth rates of cells. For example, conditions that produce enhanced protein production, metabolite production, or biochemical production can be compared.

The current method can be used to compare production of, e.g., proteins, metabolites, small molecules, or biochemicals. For example, the method can be used to compare production of a protein, such as a hormone, enzyme, growth factor, biochemical, reporter gene, or cytokine. An enzyme that can be produced includes, for example, a protease, cellulase, amylase (e.g., an α-amylase or a β-amylase), glucoamylase, xylanase, phytase, mannanase, hemicellulase, carbohydrase, hydrolase, esterase, catalase, lactase, oxidase, permease, pullulanase, laccase, lipase, reductase, isomerase, epimerase, pectinase, tautomerase, transferase, kinase, and phosphatase. In some methods, the enzyme that is produced is a protease that is subtilisin.

In some methods, the current method can be used to compare production of, e.g., a biochemical, such as a hydrocarbon or an alcohol. Exemplary hydrocarbons or alcohols that can be produced include terpenoid, hemiterpenoid, monoterpenoid, sequiterpenoid, diterpenoid, sesterterpenoid, propanediol (e.g., 1,3-propanediol), ethanol, or butanol. In some methods, the hydrocarbon that is produced is isoprene.

In some methods, a combination of growth rates and protein, metabolite, or biochemical production are compared. Strains or conditions with enhanced protein production, metabolite production, or biochemical production without decreased growth rates can be selected.

The present culture plate can incorporate different types and/or different concentrations of compounds in different wells. For example, different wells of the culture plate can be coated with different compounds and/or different concentrations. Different compounds can also be incorporated into the present culture plate by soft lithography, particularly when the culture plate consists of multiple layers or sections bonded together. For example, multiple molds each containing a single well can be made with a polymer containing a different compound in each well, and these wells can then subsequently be bonded or cured together to make a single monolithic microtiter plate. The present culture plates can thus be used for small-molecule drug screening, DNA microarrays, gene analysis, cell culturing, single cell analysis, stem cell induction, and stem cell differentiation. Some culture plates embed a cocktail of compounds into one or more wells.

The present culture plate can be used for various downstream applications. For example, the culture plate can be used for screening, process optimization studies, media optimization, additives screening and testing of media formulations, cell line development/cloning, cell culture optimization, media additives optimization, bioreactor conditions, cell banking, cell scale up, transfection, gene therapy, stem cell production and research, protein expression, sampling and process development.

Cells suitable for culturing by the present methods include bacteria, yeast, fungi and higher eukaryotic cells such as plant or animal cells. Microbial cells are preferred.

Suitable yeast cells include *Saccharomyces* sp., *Schizosaccharomyces* sp., *Pichia* sp., *Hansenula* sp., *Kluyveromyces* sp., *Prtaffia* sp., or *Candida* sp., such as *Saccharomyces cerevisiae*, *Schizosaccharomyces pombe*, *Candida albicans*, *Hansenula polymorpha*, *Pichia pastoris*, *P. canadensis*, *Kluyveromyces marxianus*, and *Phaffia rhodozyma*.

Suitable fungi cells include *Aspergillus* (e.g., *A. oryzae* and *A. niger*), species of *Saccharomyces* (e.g., *S. cerevisiae*), species of *Schizosaccharomyces* (e.g., *S. pombe*), and species of *Trichoderma* (e.g., *T. reesei*).

Suitable bacterial cells include gram-positive bacterium (e.g., *Streptomyces* and *Bacillus*) and a gram-negative bacterium (e.g., *Escherichia coli* and *Pseudomonas* sp.). Examples include strains of Bacillus (e.g., *B. lichenformis* or *B. subtilis*), strains of *Lactobacillus*, strains of *Streptococcus*, strains of *Pantoea* (e.g., *P. citrea*), strains of Pseudomonas (e.g., *P. alcaligenes*), strains of *Streptomyces* (e.g., *S. albus*, *S. lividans*, *S. murinus*, *S. rubiginosus*, *S. coelicolor*, or *S. griseus*), or strains of Escherichia (e.g., *E. coli*).

Suitable plant cells include plant cells from the family Fabaceae, such as the Faboideae subfamily, a plant cell from kudzu, poplar (such as *Populus alba* x tremula CAC35696 or *Populus alba*) (Sasaki et al., FEBS Letters 579(11): 2514-2518, 2005), aspen (such as *Populus tremuloides*), or *Quercus robur*.

Suitable algal cells include green algae, red algae, glaucophytes, chlorarachniophytes, euglenids, chromista, or dinoflagellates.

Suitable Archaea cells include cyanobacteria cell, such as cyanobacteria classified into any of the following groups based on morphology: Chroococcales, Pleurocapsales, Oscillatoriales, Nostocales, or Stigonematales.

Suitable mammalian cells include Chinese hamster ovary (CHO) cells, HeLa cells, baby hamster kidney (BHK) cells, COS cells, monoclonal antibody-producing B-cells, or any number of other immortalized cell lines available, e. g., from the American Type Culture Collection.

Suitable insect cells include, among others, various lines from the moth *Spodoptera frugiperda*, such as Sf21, and Sf9.

EXAMPLES

Example 1

Design and Construction of Slow Release Polydimethylsiloxane (PDMS) Plates

Figure 1B:
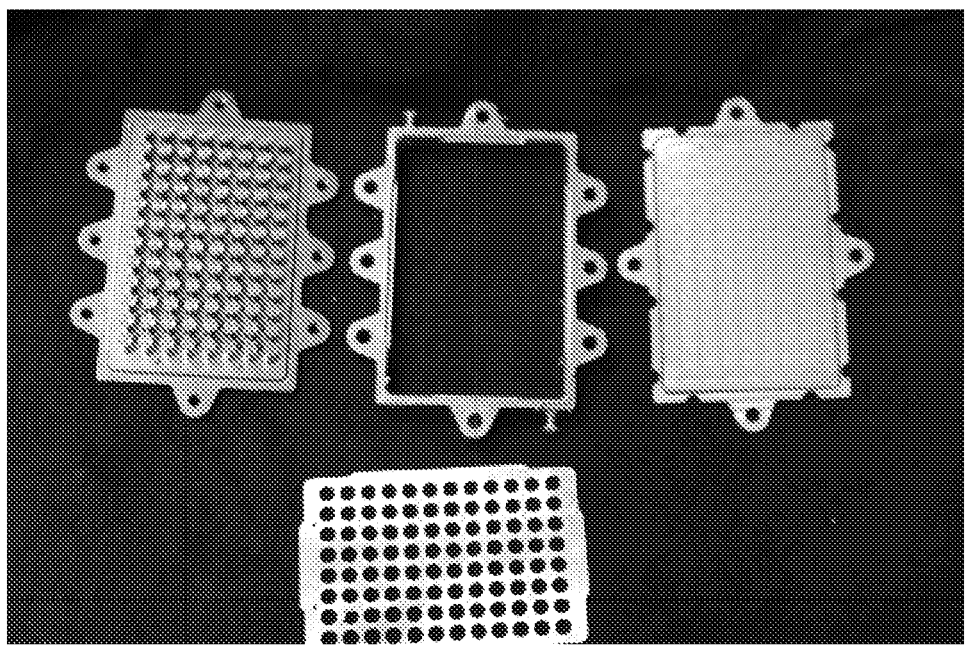
Figure 1C:
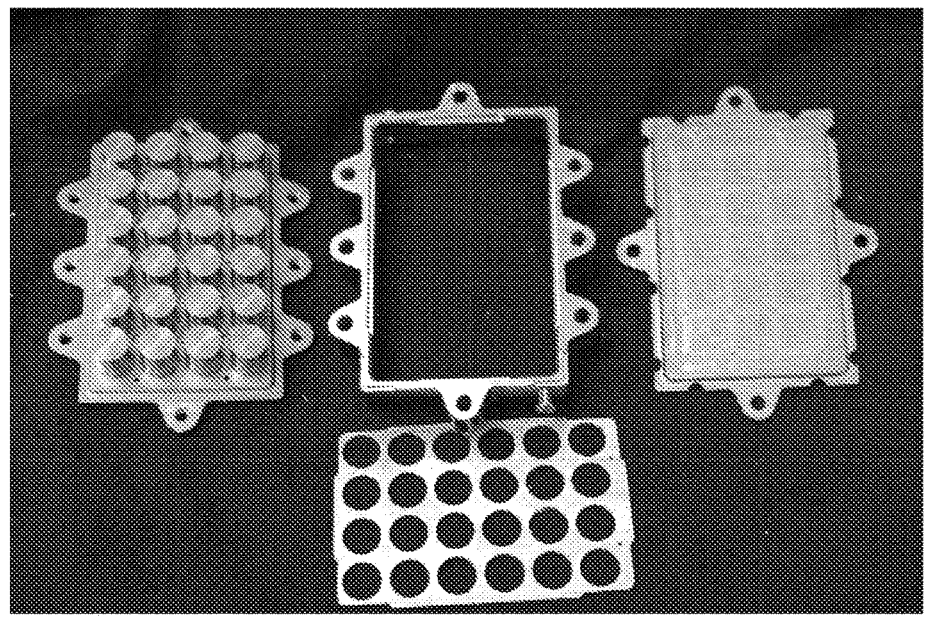

Design of PDMS plates: 96-well and 24-well molds to construct slow release PDMS elastomer plates were designed in house. Designs were drawn and manufactured using Computer Numerical Control (CNC) machining by a contract vendor. The assembled mold consists of 4 main parts. A schematic of one of the molds designed is shown in FIG. 1A. The cover, the side, the release plate, and the bottom of the plate to which the well posts are attached. In this example, only one of the 96 posts is shown. The entire mold is machined from aluminum, except for the release plate which is stainless steel. The mold is assembled using screws. Photographs of a 96 and a 24 post mold are shown in FIG. 1B and FIG. 1C, respectively.

Casting of PDMS plates: Molds were coated with a 5 micron layer of Nickel/Teflon prior to casting of PDMS within them. PDMS Sylgard Elastomer 184 was made by combining the siloxane base with the curing agent provided in the kit. The two parts were mixed together at about a 10:1 ratio and cured via an organometallic crosslinking reaction to form a solid piece of PDMS.

Materials: Dow Corning Sylgard 184 Silicone Encapsulant (Item #: 2065622,Ellsworth Adhesives, Germantown, Wis.), VWR Microprocessor controlled oven, 1330GM (VWR International, Brisbane, Calif.), NUNC 1 well dish non-treated, 127.8×85.5 mm (Nalge NUNC International, Rochester, N.Y., Part #: 267060), 24 well and 96 well molds (Screws, lid, tray, side plate), Dessicator, Spatula, Aluminum foil (Part #: 29952-172, VWR International, Brisbane, Calif.), Scale, Weigh boats, 53 µ (Catalog #: 57334-484)and 20 µ sieves (Catalog #: 57334-494) (VWR International, Brisbane, Calif.), 3M 444 Double-sided Film Tape (Model #: S-10085, Uline, Waukegan, Ill.), Edible Lactose $H_2O$ (Fine Grind 5020MFR080808, Hilmar Ingredients, Hilmar, Calif.), Cerelose Dextrose $H_2O$ (Glucose, Corn Products US, Westchester, Ill., PN 020010-102).

Mold Assembly: The release plate was inserted into the base of a 96- or 24-post (aka "well") mold. The side wall of the mold was attached to the bottom of the mold using screws. PDMS was mixed at a ratio of about 10:1 with the curing agent along with the sugar in the desired concentration. A final weight of 100 g for a 96-well plate or 110 g for the 24-well plate of PDMS, curing agent, and sugar was used. The sugar and PDMS mixture was mixed for 60 seconds and degassed in a desiccator for 20-30 minutes. The mixture was poured into a 24-well or 96-well mold and the molds were placed in the desiccator for additional 10-15 minutes. The mold plates were removed from the desiccator and allowed to sit at room temperature for about 10 minutes until all visible bubbles disappeared. The cover was secured in place with screws and the entire apparatus was wrapped in aluminum foil and flipped over allowing the cover to face down. In other cases the mold was poured and cured without using the cover. The plates were placed in an oven at 60° C. for 4 hours (up to overnight) to allow for full curing. After curing, the foil was removed and the cap unscrewed to remove the mold. The side of the casting apparatus was removed by unscrewing it from the base using a spatula. The release plate was raised from the bottom of the casting mold to force it off the well posts.

The PDMS plates were attached to corresponding rectangular NUNC™ plastic dishes, and sealed using prior to use. The PDMS plates were placed in a freezer (−20° C.) until ready to use.

Figure 1D:
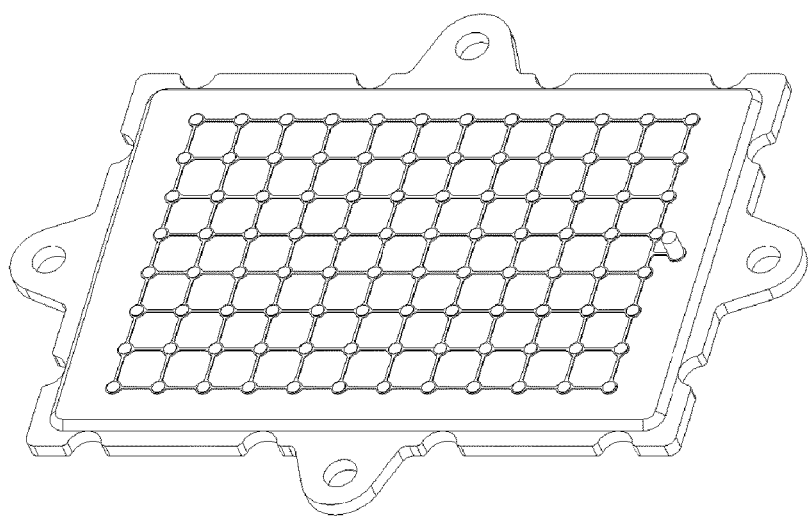

In some cases, PDMS plates were created using molds that included raised areas or "lines" machined onto the bottom of the plate to create half-channels in the molded part for delivery of gases, such as air or oxygen, to all the wells from a single input (FIG. 1D). The resulting air channels on the bottom of the PDMS-sugar plates were sealed using a double sided high-tack acrylic (3M, Minneapolis, Minn.) to allow oxygen to enrich growing cultures via air lines.

Example 2

Figure 2A:
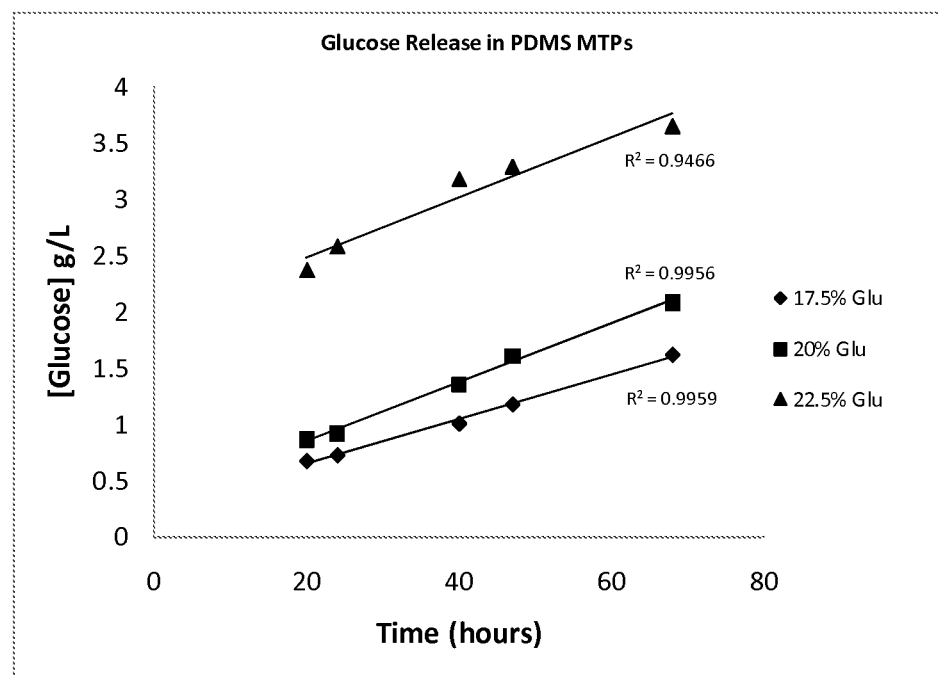
FIG. 2: (A) Glucose release in PDMS microtiter plates; (B) Glucose concentration in srMTP wells from plates molded with different concentrations of batched glucose.

Glucose Release from PDMS Microtiter Plates 24-well MTPs were cast with PDMS containing 17.5%, 20%, or 22.5% glucose as described in Example 1. Water (1 mL) was added to each well of the plate and 50 microliter aliquots were removed from each plate at 20, 24, 40, 48 and 60 hour time points and assayed for glucose concentration using the ABTS assay as described below. A linear curve fit was performed using glucose standards in the ABTS assay. By varying the percentage of sugar in the PDMS, different release rates can be achieved. The release rates remain linear at different concentrations (FIG. 2A).

Figure 2B:
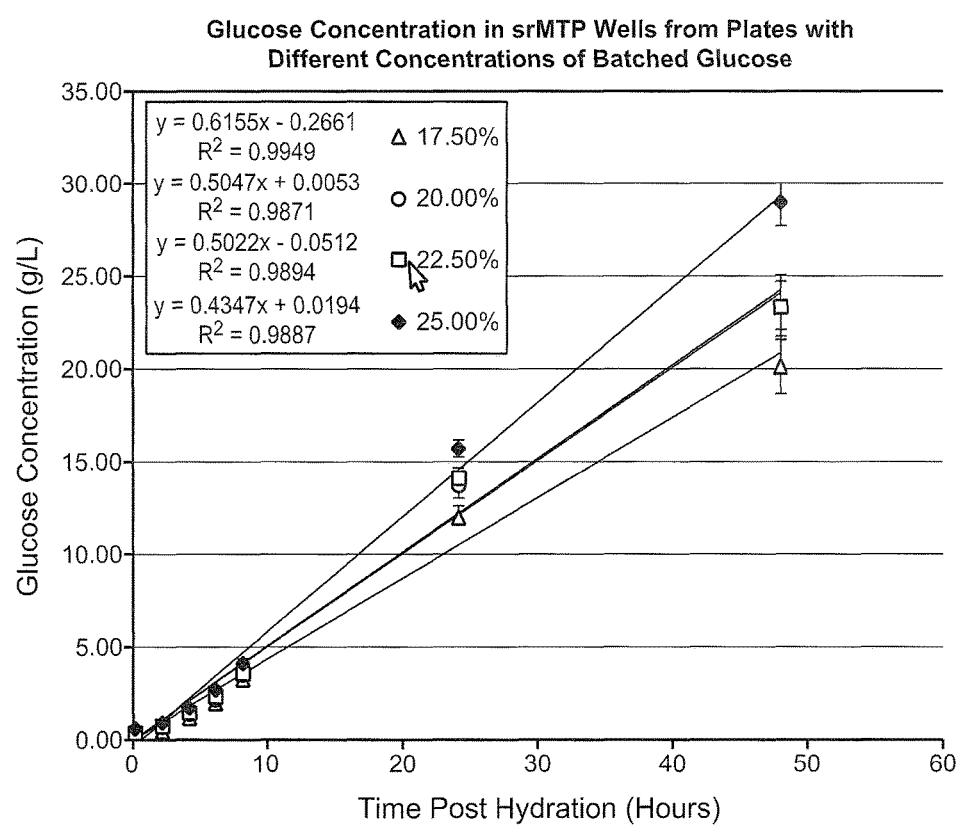

The above experiment was repeated measuring at additional timepoints. 24 well MTPs were cast with PDMS containing 17.5%, 20.0%, 22.5%, or 25.0% glucose by weight as described in Example 1. Water (1 mL) was added to each well of the plate and was then subsequently incubated at 37 degrees Centigrade for 48 hours. At 0, 2, 4, 6, 8, 24, and 48 hours, 50 microliter aliquots were removed and assayed for glucose concentration using the ABTS assay described below. A linear curve was fit using glucose standards in the ABTS assay (FIG. 2B). Glucose concentrations over time and release rates were determined by polynomial regression. Maximum concentrations of glucose were reached at the 48 hour time point with glucose concentrations reaching 20.22 g/L (at 17.5%), 23.37 g/L (at 20.0%), 23.39 g/L (at 22.5%), and 28.89 g/L (at 25.0%).

ABTS assay for glucose determination: The ABTS (2, 2'-azino-bis(3-ethylenethiazoline-6)-sulfonic acid) assay for glucose determination is based on the principle that in the presence of $O_2$, glucose oxidase catalyzes the oxidation of glucose while producing stoichiometric amounts of hydrogen peroxide ($H_2O_2$). This reaction is followed by the horseradish peroxidase (HRP) catalyzed oxidation of ABTS which linearly correlates to the concentration of $H_2O_2$. The emergence of oxidized ABTS is indicated by the evolution of a green color, which is quantified at an OD of 405 nm A mixture of ABTS powder (Sigma, #A1888-5 g 2.74 mg/mL), 0.1 U/mL HRP (100 U/mL, Sigma, #P8375) and 1 U/mL Glucose Oxidase (5379 U/mL, Genencor®) was prepared in 50 mM sodium acetate buffer, pH 5.0 and kept in the dark (substrate). Glucose standards (0, 2, 4, 6, 8, 10 nmol) were prepared in 50 mM sodium acetate buffer, pH 5.0 and 10 µl of each standard was added to 96 well flat bottom MTP in triplicate. Ten microliters of serially diluted samples were also added to the MTP. One hundred microliters of ABTS substrate solution was added to each well and the plate was placed on a spectrophotometric plate reader. The OD was measured as an endpoint reading after 15-30 minutes of incubation following quenching of the reaction with 50 mM Na Acetate Buffer, pH 5.0 containing 2% SDS.

Example 3

Growth of *Bacillus* Cells in Slow Release PDMS Plates

Figure 3A:
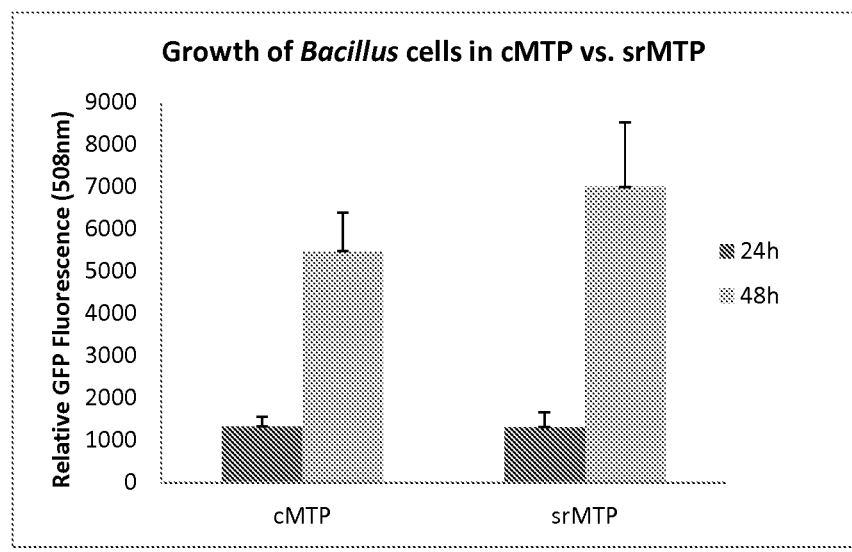
FIG. 3: (A) Growth of Bacillus cells in cMTP vs. srMTP; (B) Growth of Bacillus strain A in conventional vs. slow release PDMS 96-well microtiter plate; (C) Growth of Bacillus strain B in conventional vs. slow release PDMS 96-well microtiter plate; (D) Growth of Bacillus strain C in conventional vs. slow release PDMS 96-well microtiter plate; (E) Growth of Bacillus strain D in conventional vs. slow release PDMS 96-well microtiter plate.
Figure 3B:
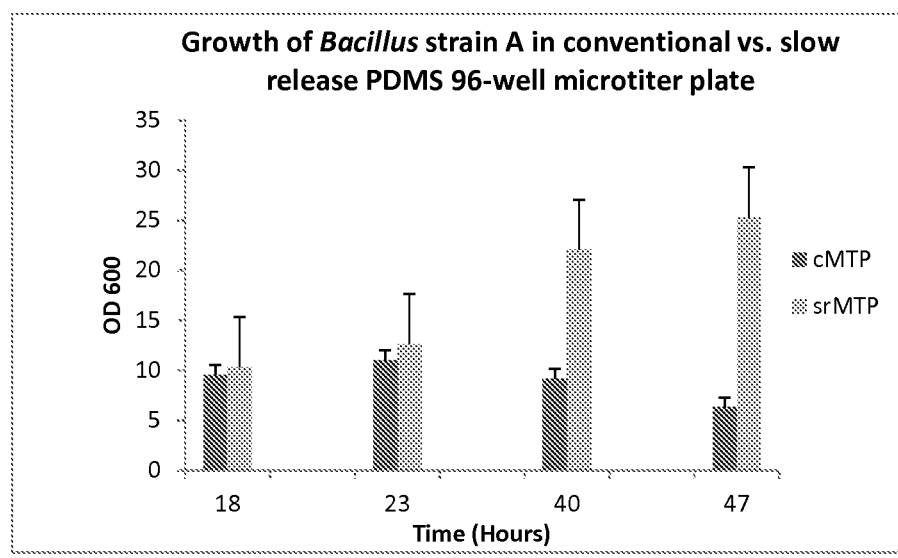
Figure 3C:
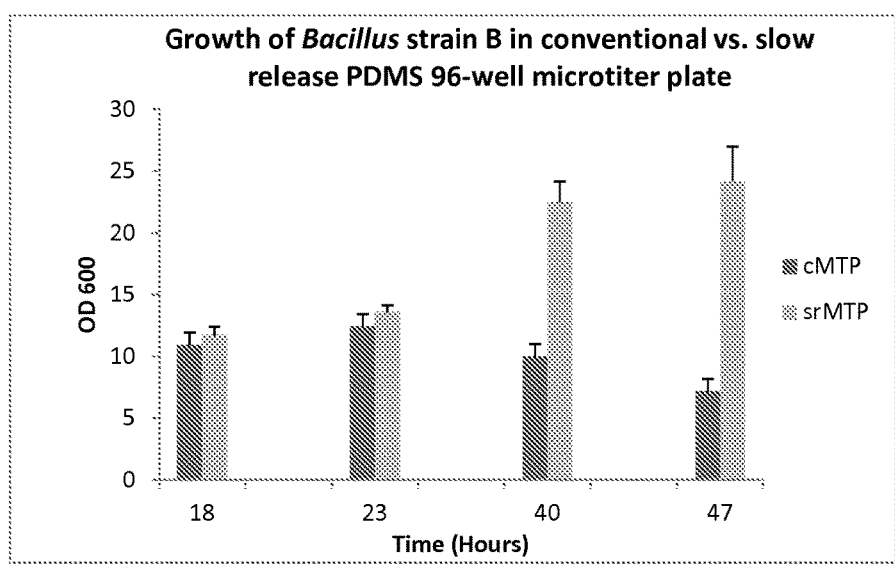
Figure 3D:
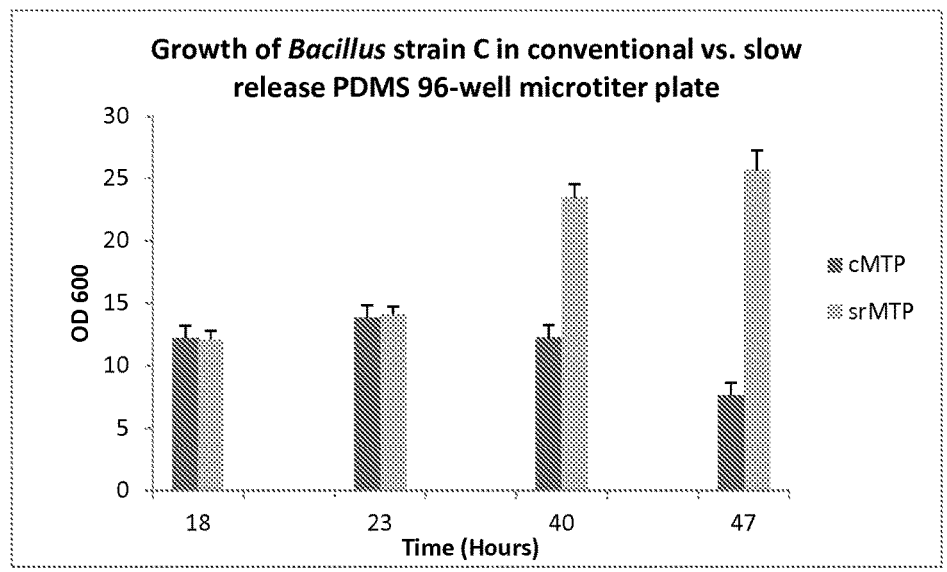
Figure 3E:
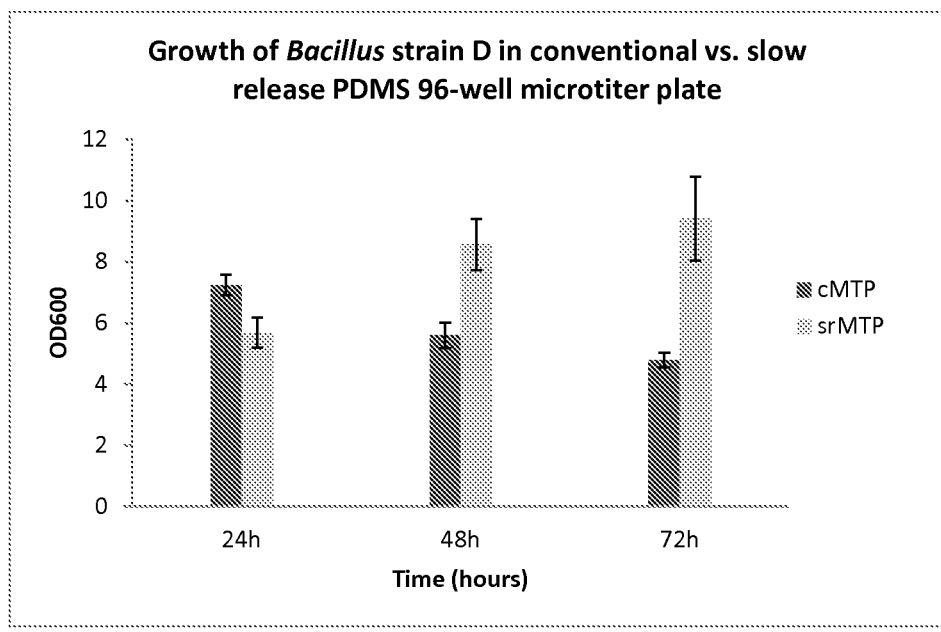

The growth of *Bacillus subtilis* cells in slow release PDMS plates was compared to that in conventional 96-well MTPs. A green fluorescent protein expressing derivative of *Bacillus subtilis* SC6.1 (also called BG3594comK) (DaprE, DnprE, degU.sup.Hy32, oppA, DspoIIE3501, amyE::xylR-PxylAcomK-phleo) was created by transformation with green fluorescence protein (GFP), behind the promoter aprE, also containing comK and a chloramphenicol marker (PaprE:PtGFPcomK-cmp). SC6.1-GFP cells were cultured for 24 and 48 hours at 37° C. at 250 rpm in cultivation medium [enriched semi-defined media based on MOPs buffer, with urea as major nitrogen source, glucose as the main carbon source, and supplemented with 1% soytone for robust cell growth] in conventional or in the same medium without added sugar in a slow-release PDMS plate containing 20% glucose. Following growth, plates were analyzed on a fluorescent plate reader (Spectramax, Molecular Devices, Foster City, Calif.) to measure GFP expression as relative fluorescence released. *Bacillus subtilis* cells were found to produce more GFP protein after 48 h of culture in this plate than in a conventional microtiter plate (FIG. 3A).

The growth of three additional *Bacillus* strains, (A, B, and C) cultured in conventional microtiter plates (cMTP) or slow release microtiter plates (srMTP) was measured at 18, 23, 40 and 47 hours (FIGS. 3B-3E). These strains are derivatives of strain SC6.1, all deleted for comK. Strains B and C also have mutations encompassed in the USPTO Application #: #20110045571—Class: 435221. Growth was also measured in an additional strain (D, also known as BG8010), at 24, 48, and 72 hours. BG8010 is a derivative strain of BG2942 (ΔnprE, degU(Hy)32, amyE::PxylRA-comK-eryR). In addition to these modifications of BG2942, deletion of the aprE, and spoIIE genes were performed using the Cre-lox recombinase system. The opp operon was deleted by introducing the phleomycin marker in the oppA locus. The resulting laboratory strain BG8010 has the following genotype ΔnprE, ΔaprE, degU(Hy)32, spoIIE312, oppA:phleoR, amyE::PxylRA-comK-eryR. (D).

Example 4

Protease Production from *Bacillus* Cells Grown in Slow Release PDMS Plates

Figure 4A:
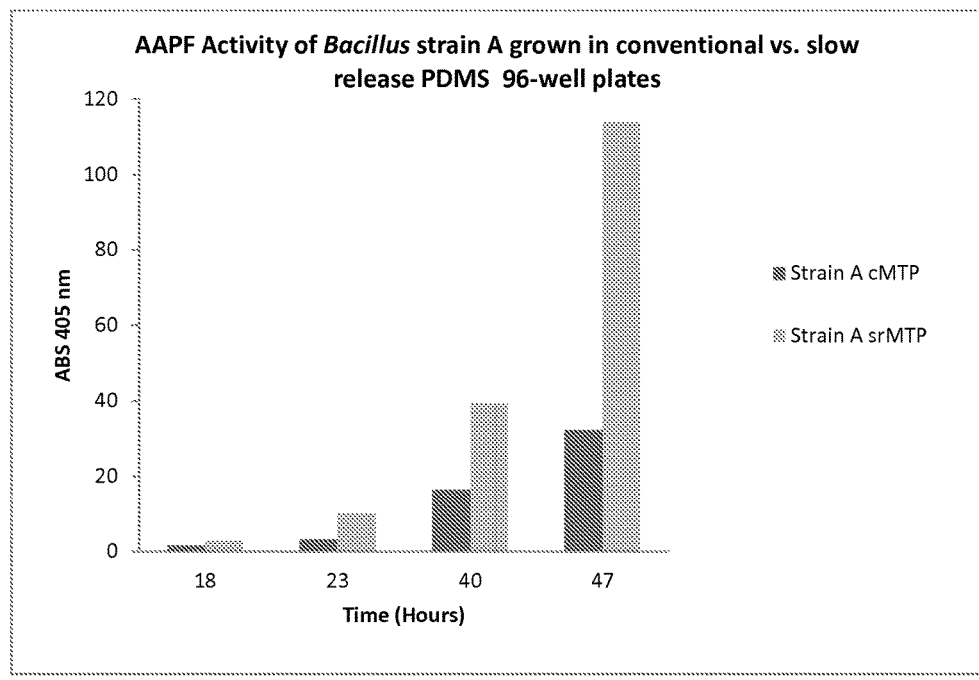
FIG. 4: (A) AAPF Activity of Bacillus strain A grown in conventional vs. slow release PDMS 96-well plates; (B) AAPF Activity of Bacillus strain B grown in conventional vs. PDMS slow release 96-well plates; (C) AAPF Activity of Bacillus strain C grown in conventional vs. PDMS slow release 96-well plates.
Figure 4B:
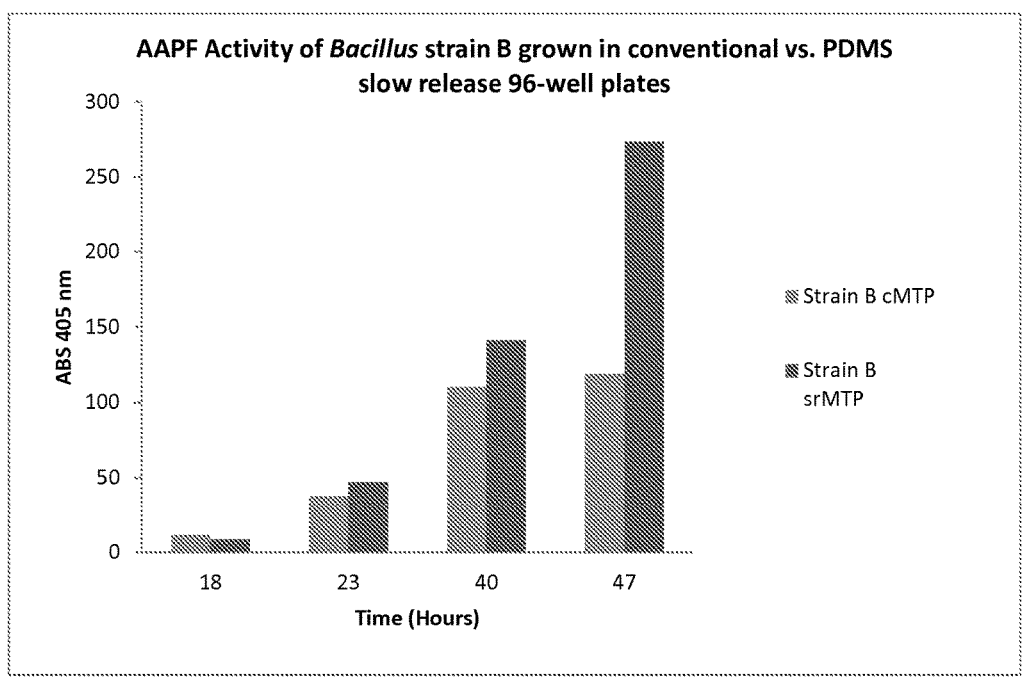
Figure 4C:
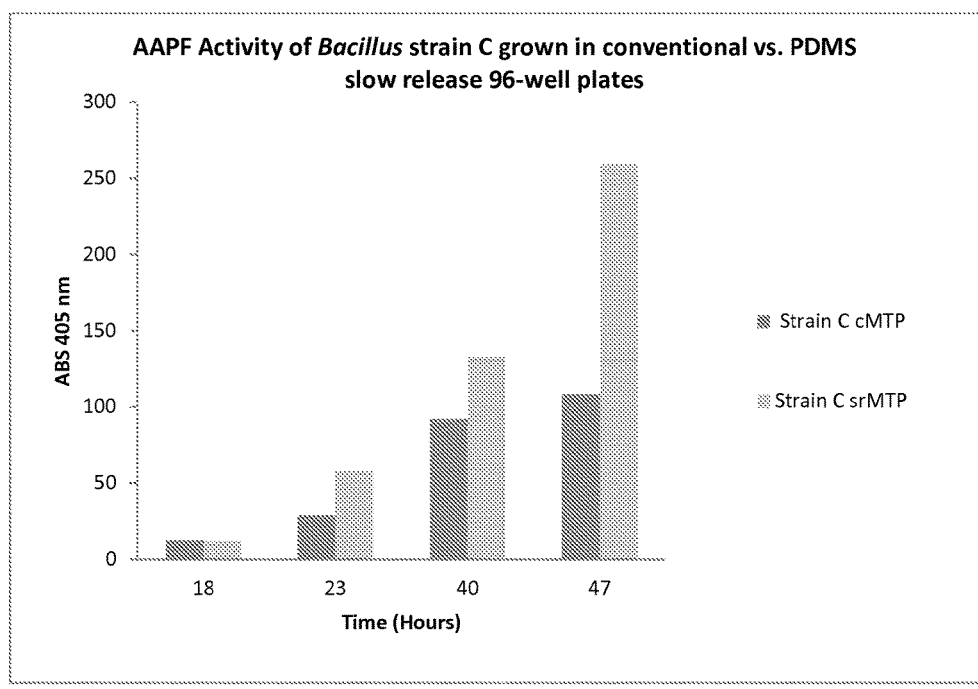

Subtilisin enzyme expression from *Bacillus* strains A, B, and C grown in either conventional (c MTP) or slow release (srMTP) microtiter plates was measured following growth for 18, 23, 40 and 47 hours using the AAPF assay as described below (FIG. 4A-C).

AAPF Assay: In order to determine protease activity, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 50 ml Tris/Ca buffer and mixed repeatedly. The assay was performed by adding 5 µl of diluted culture supernatant to each well containing 150 µl Tris dilution buffer, immediately followed by the addition of 100 µl 2 mg/ml suc-AAPF-pNA working solution. The solutions were mixed for 5 sec., and the absorbance change in kinetic mode (11 readings in 2 minutes) was read at 405 nm in an MTP reader, at 25° C. The protease activity was expressed as AU absorbance at 405 nm.

Example 5

Corn Cob Hydrolysis by *Trichoderma* Variants Grown in Slow Release PDMS Plates

In this study, glucose liberated from pretreated corn cob by *Trichoderma* variants grown in different formats was studied.

Mutated germlings of an H3A integrated *Trichoderma reesei* expression strain was prepared in accordance with the description of PCT/US2010/049849, published as WO/2011/038019, and modified to contain a GFP expression cassette containing an additional copy of the cbh1 promoter and a hygromycin resistance marker (pcbh1:gfp:hph), were sorted on the basis of GFP expression. Individual germlings from each GFP expressing library were sorted into wells (one germling per well) of microtiter plates that were grown in glycine minimal medium containing 2.4% lactose an oxygen chamber (cMTP), or in minimal media in slow-release microtiter plates (20% lactose by weight) and grown in an oxygen chamber (srMTP). All plates were grown at 28° C. for approximately 170 hours.

Figure 5:
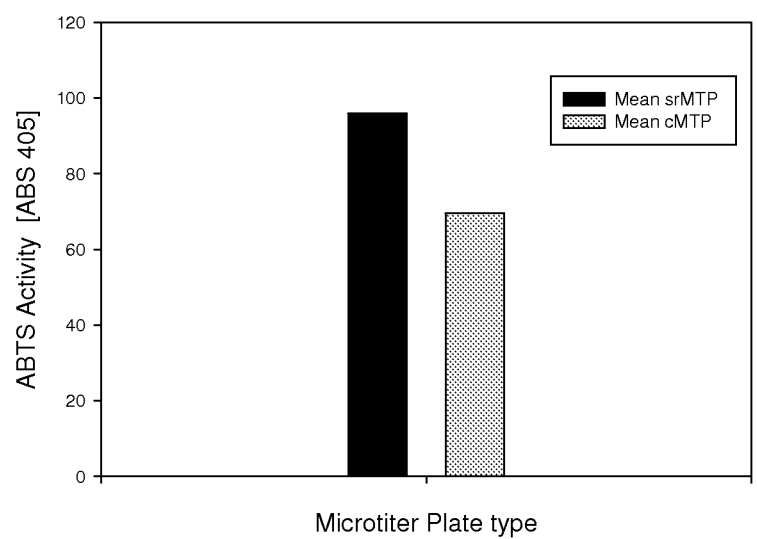
FIG. 5: Corn cob hydrolysis by a Trichoderma variant grown in cMTP vs. srMTP.

Following incubation, the supernatants from all cultures were assayed for glucose liberated from dilute ammonia pretreated corn cob (Corn cob was pretreated prior to hydrolysis according to the methods and processing ranges described in WO061109). Twenty microliters of culture supernatant and 60 µl of 50 mM sodium acetate buffer pH 5.0 was added to 70 mg of dilute-ammonia pretreated corn cob at 7% cellulose solids substrate per well. The assay plate was incubated at room temperature for 10 minutes. The assay plates were covered with aluminum plate sealers and the plates incubated at 50° C., 200 rpm, for three days. At the end of the incubation period, the saccharification reaction was quenched by adding 100 µl of 100 mM glycine buffer, pH 10.0 per well assay and the plate was centrifuged for five minutes at 3000 rpm. Ten microliters of the supernatant was assayed for glucose liberated by the ABTS assay as described in Example 2. Results are shown in FIG. 5.

Example 6

Figure 6:
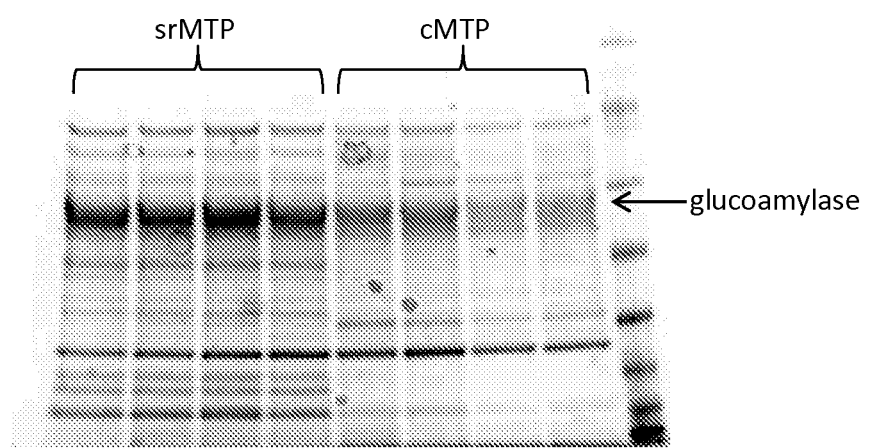
FIG. 6: A Polyacrylamide Gel Electrophoresis (PAGE) of a Trichoderma strain expressing glucoamylase grown in defined medium in a PDMS srMTP containing 20% lactose (lanes 1-4) or in a conventional microtiter plate grown in defined medium containing 2.4% lactose (lanes 5-8).

Glucoamylase Expression by a *Trichoderma* Strain Grown in Slow Release PDMS Plates The glucoamylase expression of a *Trichoderma* strain (U.S. Pat. Nos. 5,847,276 & 7,919,299) grown in defined medium in a PDMS srMTP containing 20% lactose (wt/wt) or in a conventional microtiter plate grown in defined medium containing 2.4% lactose (wt/vol) was compared by Polyacrylamide Gel Electrophoresis (PAGE). Equal volumes of culture supernatants from strains grown at 28° C., 250 rpm for ~96 hours were subjected to a reducing environment for 15 minutes at 90° C. before addition of loading dye and resolution on a 4-12 NuPage™ (Invitrogen, Carlsbad Calif.) polyacrylamide gel. The gel was stained with SimplyBlue™ (Invitrogen) and imaged (FIG. 6).

Example 7

Growth and Isoprene Production by *E.coli* Grown in Slow Release PDMS Plates

Introduction: A desire to grow and study *E. coli* strains at small scale under conditions that closely replicate the glucose-limited slow growth condition imposed in 14L (aka bioreactor fed-batch) fermentation by our project was desired. 14-L fermentations are too expensive and time consuming to generate the desired conditions for monitoring relevant high cell density behavior of our increasing number of *E. coli* strains of interest. Specifically, a condition that allowed a relatively high cell density (measuring>10 at 600 nm) and slower glucose-limited growth following more rapid glucose-excess exponential growth was sought.

The observation of interest was that strain REM H8_12 exhibited a reduced level of isoprene production during the slower growth period of 14-L fermentation compared to strain REM F2_18, where both strains produced higher and more comparable levels of isoprene during the exponential growth phase (see U.S. Prov. Pat. Appl. No. 61/426,505 filed Dec. 22, 2010). We sought to investigate this behavior in small scale, but were currently limited by small scale batch conditions employed. The slow release glucose 24-well plate described here was used to try and attain growth conditions that allow a higher cell density (measuring >10 at 600 nm) that was more similar to 14-L cell densities and that the current batch condition did not support, as well as allow slower glucose-limited growth following more rapid glucose-excess exponential growth.

The results from one of 3 experiments run with the *E. coli* strains REM H8_12, REM 14_18, and REM F2_18 are presented here and intended to reflect the success of the slow release glucose 24-well plate in achieving the small scale condition desired. Furthermore, isoprene productivity data is presented to demonstrate that the cells are still viable and producing isoprene after 44 hours of incubation within the slow release glucose 24-well plate. Similar to 14-L results, strain REM H8_12 was observed to produce less isoprene during the slower growth phase than the REM F2_18 strain. We took the results presented to suggest that the REM 14_18 strain might behave more similarly to the REM F2_18 strain than the REM H8_12 strain in 14-L fermentation during the slower glucose-limited growth phase. This was indeed found to be the case.

The ability to screen strains for this type of behavior in small scale will aid in the selection of strains to move forward to large scale 14-L fermentation as well as provide an opportunity to study the behavior and what factors influence it. This small scale alternative to 14-L provides the opportunity to assess a number of strains and/or media conditions at a time, which further adds to the time and money saved over performing 14-L fermentations.

Methods: Cells were grown overnight in 3 ml cultures at 30° C. in TM3 liquid media (see description of TM3, for example, U.S. application Ser. No. 12/335,071 and PCT/US2008/086809) supplemented to a final concentration with 0.1% yeast extract and 1.0% glucose. When appropriate, kanamycin (Kan) and/or carbenicillin (Carb) and/or spectinomycin (Spec) were added to the growth media each at 50 µg/ml. Strain REM H8_12 is described in Pct. Intl. Pub. No. WO 2010/148150 A1 and is Carb, Spec, and Kan resistant; strain REM F2_18 is described in U.S. Prov. Pat. Appl. No. 61/426,505 filed Dec. 22, 2010 and is Carb, Spec, and Kan resistant; strain REM 14_18 is of the same genotype as strain REM F2_18 with the exception that it does not harbor the additional Spec-resistant GI1.6 fldA-ispG/pCL construct (see details in U.S. Prov. Pat. Appl. No. 61/426,505 filed Dec. 22, 2010) and is Carb and Kan resistant.

Figure 7A:
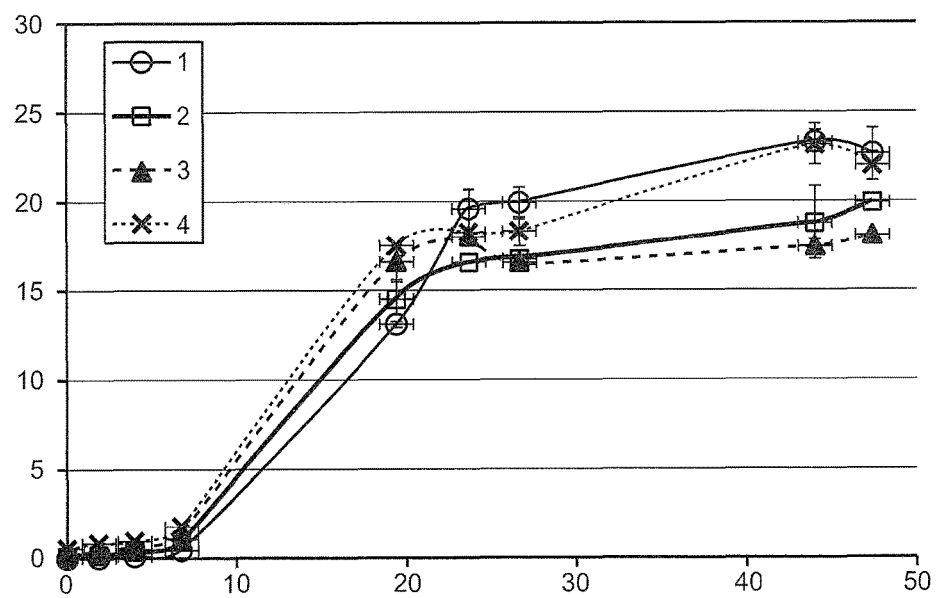
FIG. 7: (A) Growth rate of REM H8_12 in 17.5% controlled glucose release plate. The X-axis is time in hours; the Y-axis is optical density (measured at 600 nm wavelength). The average of 2 technical replicate wells is shown for each time point measured, with the standard deviation indicated by error bars. The trend lines: for 1, solid line open circles are the 3 µl inoculated wells; 2 solid line open squares are the 12 µl inoculated wells; 3 dashed line filled triangles are the 24 µl inoculated wells; 4 dashed line hatch marks are the 48 µl inoculated wells. See methods for details; (B) Growth rate of REM 14_18 in 17.5% slow glucose release plate. The X-axis is time in hours; the Y-axis is optical density (measured at 600 nm wavelength). The average of 2 technical replicate wells is shown for each time point measured, with the standard deviation indicated by error bars. The trend lines: for 1, solid line open circles are the 3 µl inoculated wells; 2 solid line open squares are the 12 µl inoculated wells; 3 dashed line filled triangles are the 24 µl inoculated wells; 4 dashed line hatch marks are the 48 µl inoculated wells. See methods for details; (C) Growth rate of REM F2_18 in 17.5% slow glucose release plate. The X-axis is time in hours; the Y-axis is optical density (measured at 600 nm wavelength). The average of 2 technical replicate wells is shown for each time point measured, with the standard deviation indicated by error bars. The trend lines: for 1, solid line open circles are the 3 µl inoculated wells; 2 solid line open squares are the 12 µl inoculated wells; 3 dashed line filled triangles are the 24 µl inoculated wells; 4 dashed line hatch marks are the 48 µl inoculated wells. See methods for details; (D) Specific productivity of isoprene at 44 hours. The X-axis depicts strain labels: A represents REM H8_12; B represents REM I4_18; C represents REM F2_18. The Y-axis indicates isoprene ug/L/OD/Hr (specific productivity). The average of 2 technical replicate wells is shown for the 44 hour time point measured for the 3 µl inoculum wells, with the standard deviation indicated by error bars.
Figure 7B:
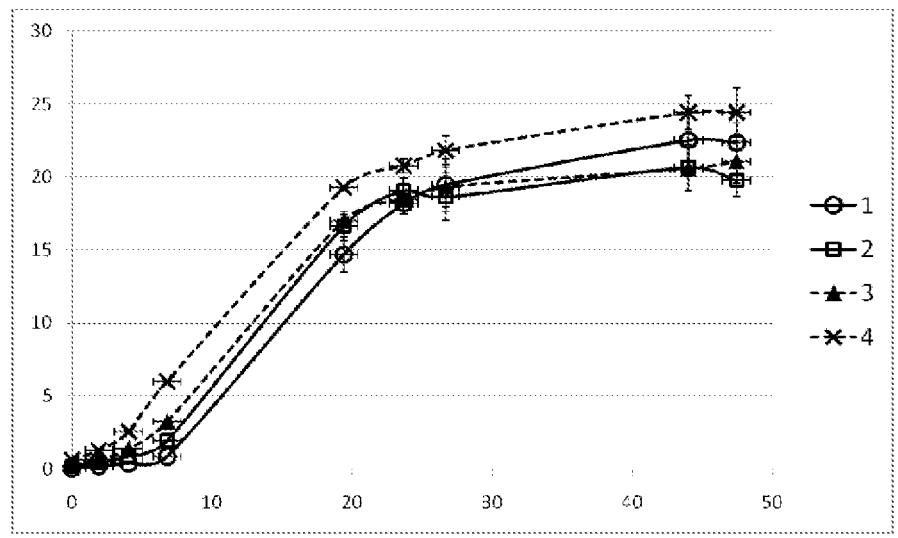
Figure 7C:
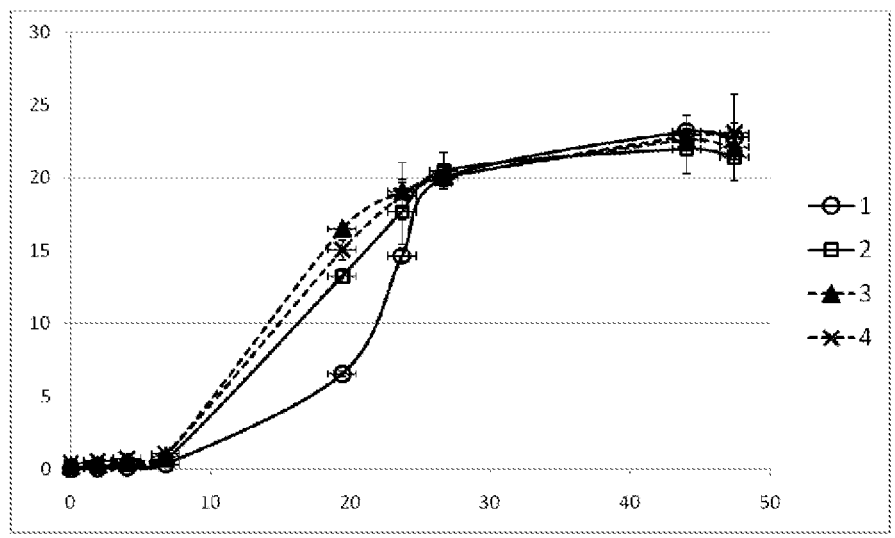

In the morning cultures were diluted to an optical density (OD) of approximately 0.4 to 0.6 measured at 600 nm within 5 ml of fresh TM3 liquid media containing a final concentration of 0.1% yeast extract, 1.0% glucose, and 25 uM IPTG along with the appropriate antibiotics. The cells were allowed to grow at 30° C. for roughly 2.5 hours after which time the cells were harvested by centrifugation at room temperature in 15 ml Falcon tubes at 5,000 rpm for 10 min. (eppendorf Centrifuge 5840 R 15 amp version). The resulting supernatants were discarded and the cell pellets suspended in 160 µl of TM3 liquid media containing 0.1% yeast extract without glucose (targeting a final cell suspension volume of 180 µl). 3 µl, 12 µl, 24 µl, and 48 µl of each of the cultures was inoculated into 2 individual wells (allowing technical replicates for each of the 4 inoculums; 3 strains with 4 inoculums each in duplicate yields 24 wells) of a 17.5% slow glucose release 24-well plate (wt/wt) that had been pre-incubated for approximately 20 hours with 1.2 ml TM3 liquid media containing 0.1% yeast extract without glucose and the appropriate antibiotics in each well that was shaken at 250 rpm at 30° C. within an EnzyScreen™ cassette inside a model AJ150 ATR Inc. incubator. Immediately preceding inoculation a final concentration of 200 µM IPTG and an additional 50 µg/L carbenicillin was added to each of the 24 wells. Bacterial growth was monitored by OD over the course of 2 days (FIGS. 7A-C).

Figure 7D:
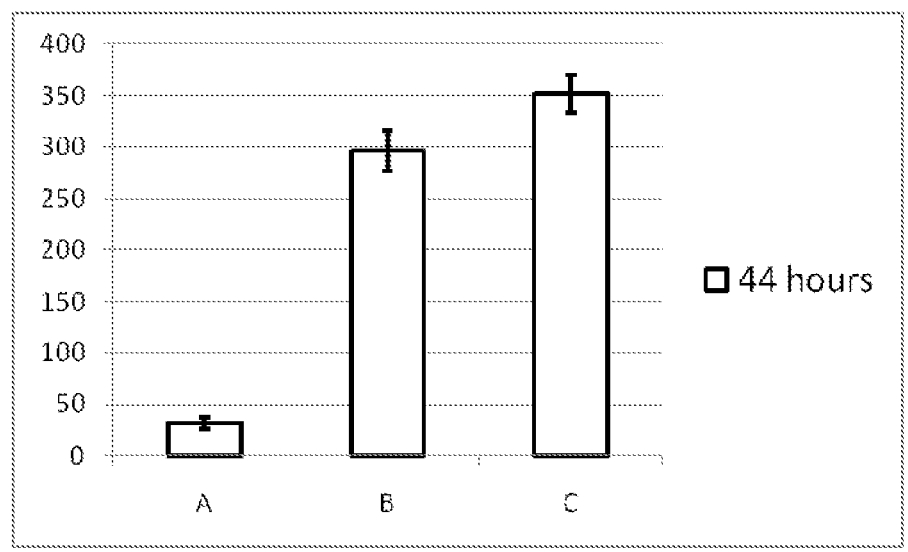

At the penultimate time point (approximately 44 hours) specific productivity of isoprene was determined for each of the 3 µl inoculum wells (FIG. 7D). Calculation of the specific productivity of isoprene and the methods used to determine such can be found in US20110046422.

Example 8

Glucoamylase Activity Comparison Between cMTP vs srMTP

Figure 8:
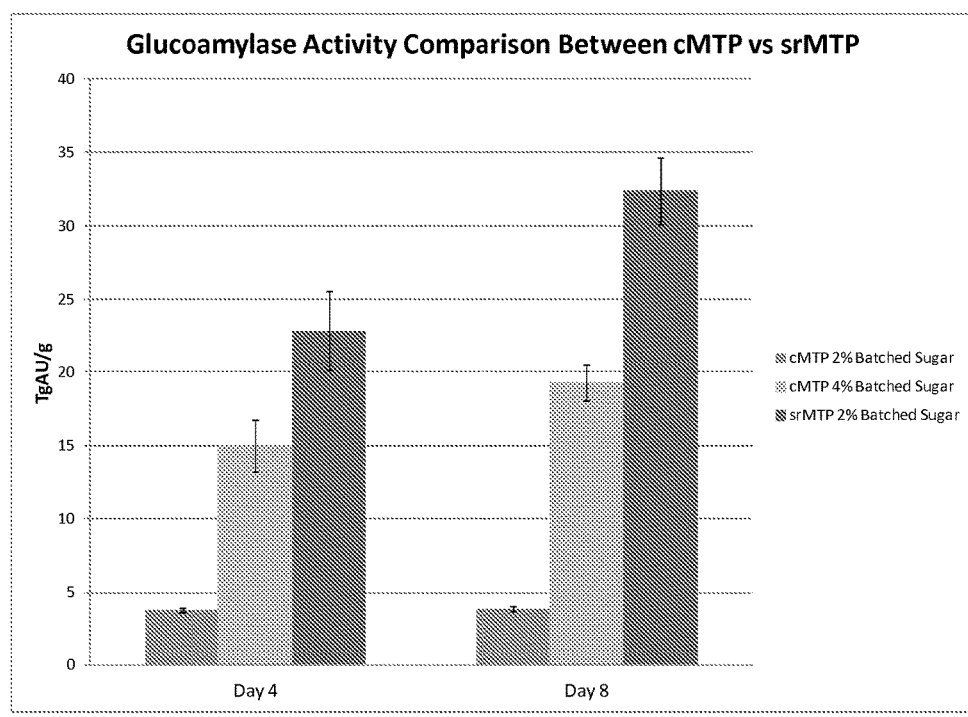
FIG. 8: Glucoamylase activity comparison between cMTP vs srMTP.

This Trichoderma reesei strain was evaluated for glucoamylase activity between conditions in a cMTP and a srMTP (FIG. 8). The media used contained either 2 or 4% batched sugar. The strain was grown for a total of 8 days in a shaking incubator at 250 RPM, 5 cm throw, 28° C., 85% humidity. For both time points, a 200 µl sample was taken from each well (8 wells in total) and put into a 96 well filter plate.

For the glucoamylase assay, the filtered supernatant was then diluted 5 fold with 100 mM sodium acetate buffer pH 4.3. 20 µl of this was added to 100 µl of substrate solution and incubated at room temperature for 10 minutes. This reaction is stopped by adding borax stop buffer pH 9.2 and analyzed at an OD of 405 nm The activity is compared to a standard that has measured activity. All 8 wells were averaged from each condition.

All media components are the same between the 3 conditions above with the exception of the cMTP 4% batched sugar, which has twice as much sugar as the others. The cMTP 2% batched sugar and the srMTP 2% batched sugar are the same conditions and differ only by type of plate. The srMTP was made with 20% lactose w/w with PDMS.

The srMTP shows increase in glucoamylase activity compared to both cMTP conditions. There is approximately an 8 fold increase in activity compared to cMTP 2% batched sugar and almost 2 fold increase in activity with cMTP 4% batched sugar (FIG. 8).

Example 9

Protein Production Comparison Between cMTP vs srMTP

Figure 9A:
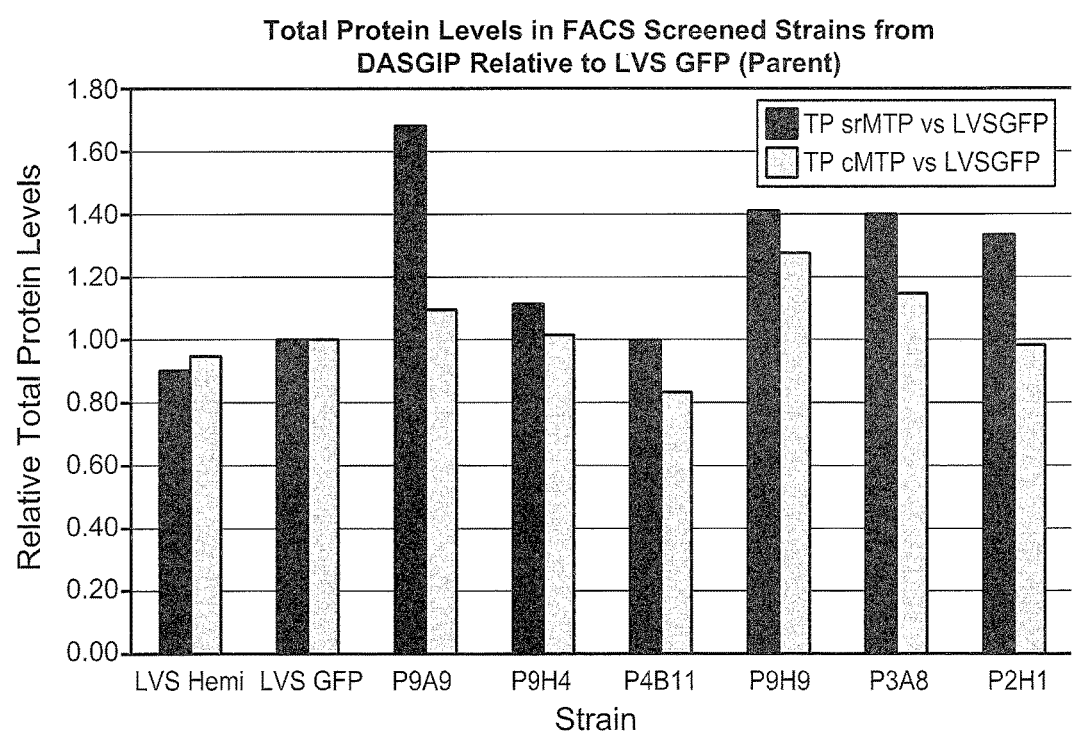
FIG. 9: (A) Total protein levels in FACS screened strains from DASGIP relative to LVS GFP (parent); (B) GFP levels in FACS screened strained from DASGIP relative to LVS GFP (parent).
Figure 9B:
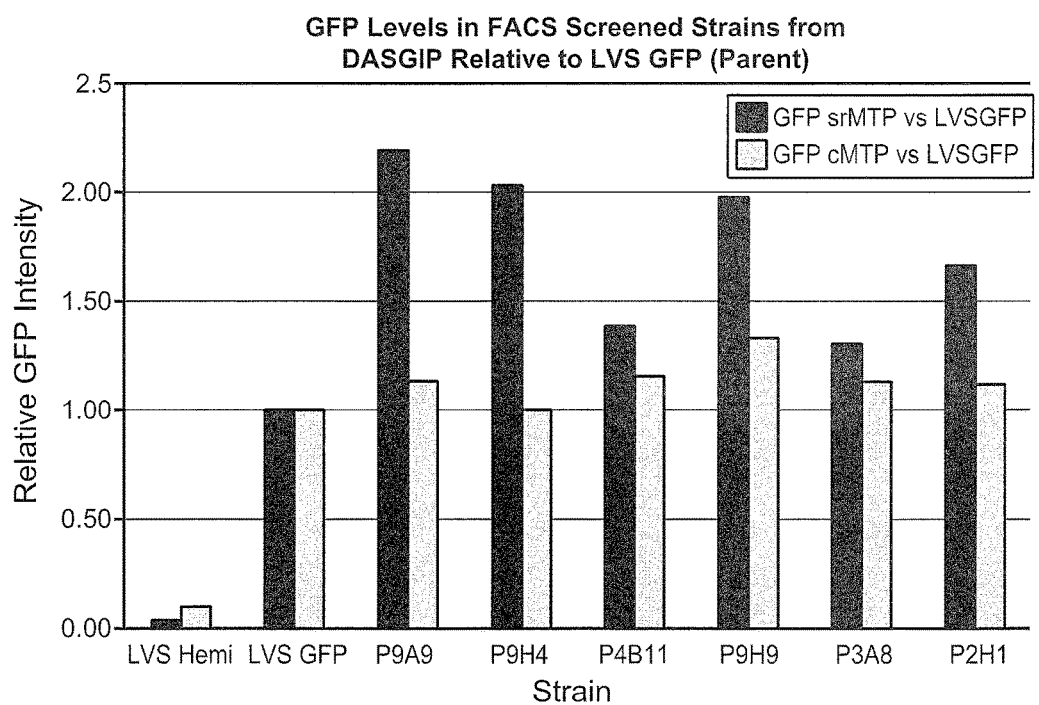

This example describes some screening data comparing total secreted protein in one example (FIG. 9A), and GFP in another example (FIG. 9B). In this case, the parent strain is LVS GFP, which was mutagenized, grown in a fed batch fermenter (production environment) and then FACS-sorted based on high GFP expression. Individual variants were sorted into and cultured in conventional 96W plates, and measured for GFP, total protein and enzyme activity. The best candidates were then transferred in parallel to conventional 24W plates and controlled-release (lactose) plates and cultured for 6 days, with controls (LVS Hemi is the grandparent strain, LVS GFP is the parent strain (i.e. unscreened), which is LVS hemi with GFP on the cbhl promoter. The variants include P9A9, P9H4, P4B 11, P9H9, P3A8, and P2H1. More significant differences between the parent and variants were observed when candidates were grown in a controlled release format (FIGS. 9A-B).

Example 10

Correlation Between Fed-Batch Fermenters and Controlled Release MTPs

Figure 10:
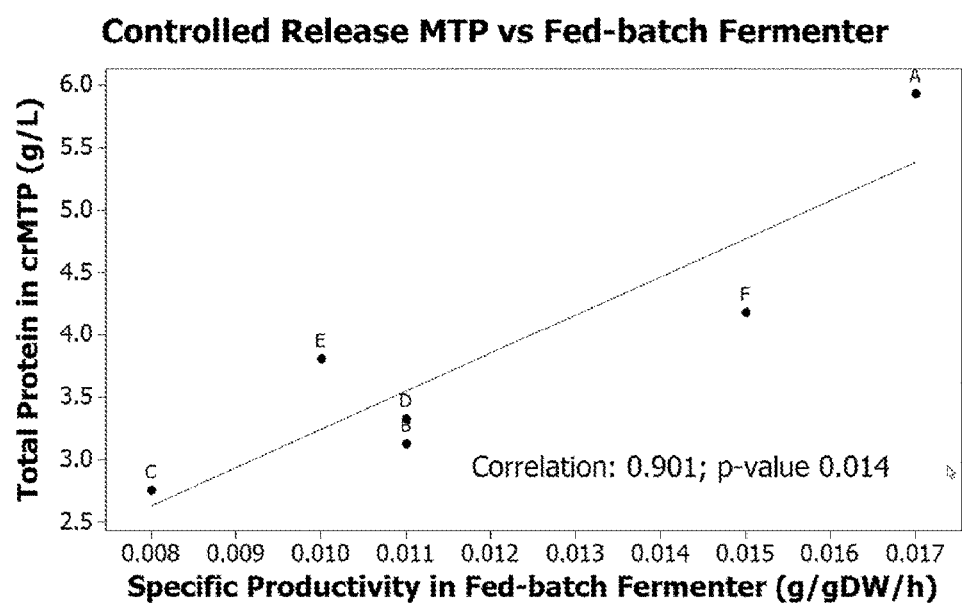
FIG. 10: Correlation between fed-batch fermenters and controlled release microtiter plates.

Six strains of Trichoderma reesei with predetermined specific productivity (grams of protein produced per gram dry cell weight per hour) were compared to the average of 4 replicate wells of a 24 well, 20% lactose (w/w) PDMS plate for 48 h (FIG. 10). Protein concentrations were determined by the Biuret assay and compared to a know standard. The Pearson correlation value was determined using Minitab software.

To determine the degree of correlation between total protein produced in controlled release microtiter plates to specific productivity in fed-batch fermenters, six trichoderma strains ("A", "B", "C", "D", "E", & "F"), were chosen. Specific feed rate values were calculated for the fed-batch fermenters. Fermentation broth was removed from growing cultures of the six tester strains at approximately 4 h intervals, and total protein and dry cell weight were determined Total protein concentration in grams per liter was determined using the Biuret assay on a Konelab Chemistry Analyzer (Thermo Scientific, Waltham, Mass.). The principle of the Biuret assay is as follows; Under alkaline conditions the reaction of cupric ions with protein molecules produces a colorful reaction. Protein serum forms a violet complex with $Cu+2$ ions. The intensity of this color is proportional to the amount of protein in the sample when compared to a standard of known concentration. Briefly, the Konelab instrument combines fermentation broth, and Total Protein Reagent (Cat. No. T7528, Pointe Scientific Inc.), in appropriate ratios. Readings are compared to a known standard (Total Protein Standard, Cat. No. T7528-STD), to determine protein concentration. Dry cell weight is determined by drying 2.5 g of fermentation broth on a filter paper using an Omnimark μWave Instrument (Sartorius, Bohemia, N.Y.). Briefly, the broth sample is vortexed and 2.5 g is weighed into a 50 mL test tube, and then transferred to a 4-inch glass-quartz filter pad, vacuum dried briefly, while rinsing with 20 mL of deionized water. The quartz pad containing partially dried fermentation broth is dried and weighed on the Omnimark Instrument. The dry cell weight in grams is reported by the instrument and then converted into grams per liter by multiplying the final weight by 1000 g/mL and dividing by 2.5 g.

For the controlled release microtiter plate samples, spores from the six example strains were transferred from culture plates to fermentation medium using a sterile cotton swab. A volume of 1.25 mL of media plus spores were added to wells of a 20% lactose controlled release MTP in quadruplicate. At regular timepoints, 100 μL of fermentation broth was removed for the Biuret assay, using the same reagents indicated above (Pointe Scientific, Inc). For controlled release MTP samples, a Hamilton Microlab Star robot was used to combine fermentation broth and Total Protein Standard, to Total Protein Reagent.

Statistics for correlation between specific productivity in fed-batch fermentations, and total protein at various timepoints (only the 48 h timepoint is shown in the example above) were computed using the Correlation function in Minitab software (version 16, Minitab, Inc., State College, Pa.), which reports the Pearson product—moment correlation coefficient, where a value of 1 indicates perfect correlation.

All patent filings, other publications, accession numbers and the like cited above are incorporated by reference in their entirety for all purposes to the same extent as if each individual item were specifically and individually indicated to be so incorporated by reference. If different variants of a sequence are associated with an accession number at different times, the version associated with the accession number at the filing date of this application is meant. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

What is claimed is:

1. A culture plate having a culture well, wherein the plate is made of a polymer incorporating a culture component releasable into culture media in the well, wherein the culture plate and the culture well consists essentially of the polymer incorporating the culture component and wherein the plate is a unitary piece formed from the polymer incorporating the culture component, wherein the polymer is formed by polymerization of a monomer in a mold.

2. The culture plate of claim 1, which is a microtiter plate with a plurality of wells.

3. The culture plate of claim 1, which has at least 24 wells.

4. The culture plate of claim 1, which has at least 96 wells.

5. The culture plate of claim 1, wherein the culture component is a nutrient.

6. The culture plate of claim 5, wherein the nutrient is a sugar.

7. The culture plate of claim 6, wherein the sugar is glucose.

8. The culture plate of claim 7, wherein the concentration of glucose is 15%-25%.

9. The culture plate of claim 7, wherein the concentration of glucose is 17.5%-22.5%.

10. The culture plate of claim 7, wherein the concentration of glucose is 20%.

11. The culture plate of claim 1, wherein the culture component is an antibiotic or buffer.

12. The culture plate of claim 1, wherein the polymer is a silicone polymer.

13. The culture plate of claim 1, wherein the polymer is polydimethylsiloxane (PDMS).

14. The culture plate of claim 1, wherein the one or more wells are connected to air lines molded into the culture plate.

15. The culture plate of claim 1, wherein the culture plate has a monolith structure.

16. A method of culturing a cell, comprising culturing the cell in a well of a culture plate of claim 1, whereby the culture component is released into the well as the cell is cultured.

17. The method of claim 16 wherein the culture media is free of the culture component except as released into the culture media from the polymer.

18. The method of claim 16, wherein the culture component is released over at least 24 hr.

19. The method of claim 16, wherein the culture component is released over at least 48 hr.

20. The method of claim 16, wherein the culture component is released linearly over at least 2 hr.

21. The method of claim 16, wherein the culture component is released linearly over at least 8 hr.

22. The method of claim 16, further comprising transferring the culture from the well into a larger volume culture.

23. The method of claim 22, wherein the larger volume culture is a fed-batch culture or a batch culture.

24. A method of culturing a plurality of cells, comprising culturing the plurality of cells in a plurality of wells in a microtiter plate of claim 2, whereby the culture component is released into the plurality of wells as the plurality of cells are cultured.

25. The method of claim 24, further comprising comparing production of a protein or other metabolite by the plurality of cells, and/or comparing the growth rates of the plurality of cells, from the plurality of wells.

26. The method of claim 25, further comprising selecting a cell based on above average growth rate or above average production of a protein or other metabolite by the plurality of cells.

27. The method of claim 25, wherein growth rate or protein/metabolite production of different strains or variants of cells is compared.

28. The method of claim 25, wherein growth rate or protein/metabolite production by the plurality of cells in different culture media is compared.

* * * * *